United States Patent [19]

Budzinski et al.

[11] 4,368,067

[45] Jan. 11, 1983

[54] HERBICIDAL SULFONAMIDES

[75] Inventors: John C. Budzinski, West Chester, Pa.; George Levitt, Wilmington, Del.

[73] Assignee: E. I. Du Pont de Nemours and Company, Wilmington, Del.

[21] Appl. No.: 244,172

[22] Filed: Mar. 25, 1981

Related U.S. Application Data

[63] Continuation-in-part of Ser. No. 144,856, Apr. 29, 1980, abandoned.

[51] Int. Cl.³ .................. A01N 43/02; C07D 239/22; C07D 491/04; C07D 251/16
[52] U.S. Cl. ............................ 71/92; 71/90; 71/93; 544/208; 544/212; 544/218; 544/278; 544/312; 544/320; 544/321; 544/330; 544/331; 544/332; 544/334; 546/280; 548/550; 548/556
[58] Field of Search ............... 544/320, 321, 331; 71/92

[56] References Cited

U.S. PATENT DOCUMENTS

| | | | |
|---|---|---|---|
| 4,169,719 | 10/1979 | Levitt | 544/331 |
| 4,214,890 | 7/1980 | Levitt | 544/321 |
| 4,231,784 | 11/1980 | Levitt | 71/92 |

*Primary Examiner*—Donald G. Daus
*Assistant Examiner*—James H. Turnipseed

[57] ABSTRACT

Pyrrole sulfonamides are useful as agricultural chemicals.

36 Claims, No Drawings

HERBICIDAL SULFONAMIDES

RELATED APPLICATION

This application is a continuation-in-part of my copending application U.S. Ser. No. 144,856, filed Apr. 29, 1980 now abandoned.

BACKGROUND OF THE INVENTION

This invention relates to pyrrole sulfonamides and in particular their use as agricultural chemicals and particularly as herbicides.

U.S. Pat. No. 4,127,405 teaches compounds which are useful for controlling weeds in wheat having the formula

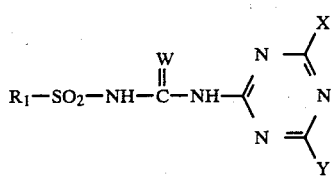

wherein $R_1$ is

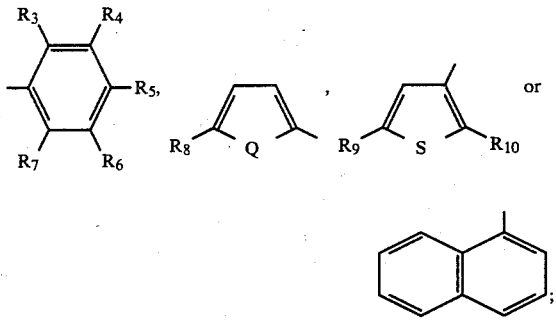

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

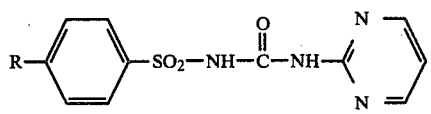

wherein R=H, halogen, $CF_3$ or alkyl.

Logemann et al. Chem. Ab., 53, 18052 g (1959), disclose a number of sulfonamides, including uracil derivatives and those having the formula:

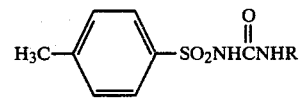

wherein R is butyl, phenyl or

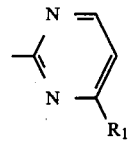

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

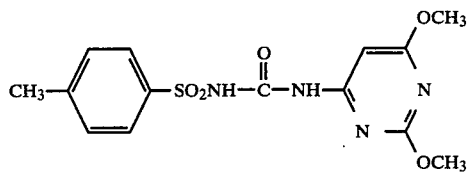

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

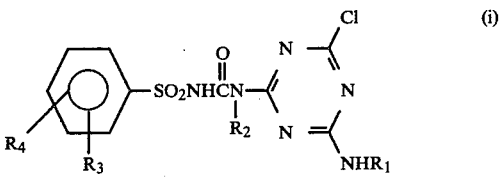

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974),

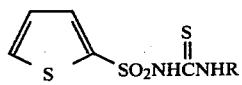

wherein R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetaion is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, to a process for preparing them, to compositions containing them and to the methods of using them as broad spectrum herbicides as well as pre-emergence and post-emergence selective herbicides and plant growth regulants.

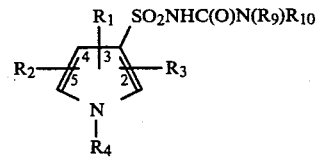

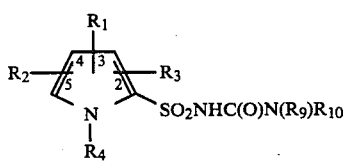

wherein
$R_1$ is H, $C_1-C_4$ alkyl, $NO_2$, CN, $C(O)CCl_3$, $SO_2R_{11}$, $C(O)R_5$ or $CO_2H$;
$R_2$ is H or $C_1-C_4$ alkyl;
$R_3$ is H, $C_1-C_4$ alkyl, Cl or Br;
$R_4$ is H, $C_1-C_4$ alkyl, cyanoethyl, $C_5-C_6$ cycloalkyl, benzyl, phenyl substituted with Cl or $NO_2$, or $C(O)R_6$;
$R_5$ is $C_1-C_4$ alkyl or $C_1-C_4$ alkoxy;
$R_6$ is $C_1-C_4$ alkyl, $C_1-C_4$ alkoxy, or $NR_7R_8$;
$R_7$ and $R_8$ are independently $C_1-C_2$ alkyl;
$R_9$ is H, $CH_3$ or $OCH_3$;
$R_{11}$ is $C_1-C_4$ alkyl;
$R_{10}$ is

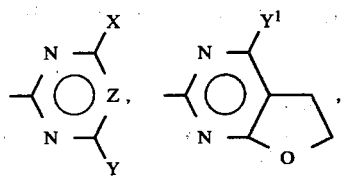

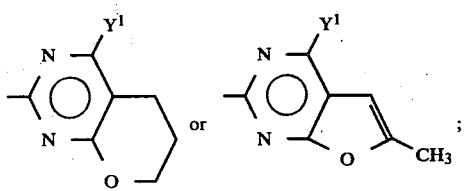

X is $CH_3$ or $OCH_3$;
Y is H, $CH_3$, $OCH_3$, $OCH_2CH_3$, $OCH_2CF_3$, Cl, $CH_2OCH_3$, $CH_2OCH_2CH_3$ or $CF_3$;
$Y^1$ is H, $CH_3$, $OCH_3$, Cl or $OCH_2CH_3$; and
Z is CH, N, $CCH_3$ $CCH_2CH_3$, $CCH_2CH_2Cl$, CCl, CBr or CF;
and their agriculturally suitable salts; provided that
(1) When $R_4$ is $C(O)R_6$, t-butyl or phenyl substituted with Cl or $NO_2$, then $R_1$ is H or $C_1-C_4$ alkyl and $R_1$, $R_2$ and $R_3$ cannot be s-butyl or isopropyl;
(2) $R_1$, $R_2$, $R_3$ and $R_{11}$ cannot be t-butyl;
(3) in Formula Ia, when $R_1$ is $NO_2$, then $R_1$ cannot be in the 5-position;
(4) in Formula Ia, when $R_1$ is not in the 5-position, $R_2$ and $R_3$ are other than H, and $R_1$ must be other than H unless both $R_2$ and $R_3$ are H;
(5) in Formula Ia, $R_3$ cannot be Cl or Br;
(6) in Formula Ib, $R_1$ cannot be $C(O)CCl_3$; and
(7) in Formula Ib, when $R_3$ is Cl or Br, then $R_3$ is in the 3-position and $R_1$ is in the 5-position and $R_1$ cannot be H or $C_1-C_4$ alkyl.

Preferred for their higher herbicidal activity and/or their more favorable ease of synthesis are:
(1) Compounds of the generic scope wherein $R_9$ is H or $CH_3$;
(2) Compound of the Preferred (1) wherein $R_{10}$ is

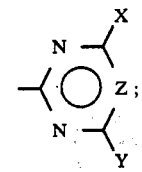

(3) Compounds of the Preferred (2) wherein
Z is CH or N;
$R_5$ is $C_1-C_4$ alkoxy;
$R_2$ is H;
$R_4$ is H, $C_1-C_4$ alkyl or benzyl;
(4) Compounds of the Preferred (3), of Structure Ia, wherein $R_1$ is H, $C_1-C_4$ alkyl or $COR_5$;
(5) Compounds of the Preferred (3), of Structure Ib, wherein $R_1$ is H, $C_1-C_4$ alkyl, $NO_2$ or $COR_5$;
(6) Compounds of the Preferred (4) wherein $R_1$ is in the 5 position;
(7) Compounds of the Preferred (5) wherein $R_1$ is H, $NO_2$ or $COR_5$; and
(8) Compounds of the Preferred (6) or (7) wherein Y is $CH_3$, $OCH_3$ or $OCH_2CH_3$.

Specifically preferred for highest herbicidal activity and/or greatest ease of synthesis are the following compounds:

N-[(4,6-dimethylpyrimidin-2-yl)aminocarbonyl]-2,5-dimethyl-1H-pyrrole-3-sulfonamide;

N-[(4,6-dimethylpyrimidin-2-yl)aminocarbonyl]-1H-pyrrole-2-sulfonamide;

N-[(4-methoxy-6-methylpyrimidin-2-yl)aminocarbonyl]-1H-pyrrole-2-sulfonamide;

N-[(4-methoxy-6-methyl-1,3,5-triazin-2-yl)aminocarbonyl]-2,5-dimethyl-1H-pyrrole-3-sulfonamide;

N-[(4,6-dimethylpyrimidin-2-yl)aminocarbonyl]-1-methyl-1H-pyrrole-X-sulfonamide; (X indicates mixtures of pyrrole-2- and pyrrole-3-sulfonamides);

N-[(4,6-dimethylpyrimidin-2-yl)aminocarbonyl]-1-(phenylmethyl)-1H-pyrrole-X-sulfonamide; (X indicates mixtures of pyrrole-2- and pyrrole-3-sulfonamides);

X-[((4,6-dimethylpyrimidin-2-yl)aminocarbonyl)aminosulfonyl]-1-methyl-1H-pyrrole-2-carboxylic acid, methyl ester; (X indicates mixtures of 4- and 5-substituents);

N-[(4,6-dimethylpyrimidin-2-yl)aminocarbonyl]-X-nitro-1H-pyrrole-2-sulfonamide; (X indicates mixtures of 3- and 4-substituents);

4-[((4,6-dimethylpyrimidin-2-yl)aminocarbonyl)aminosulfonyl]-1H-pyrrole-2-carboxylic acid, methyl ester;

5-[((4,6-dimethylpyrimidin-2-yl)aminocarbonyl)aminosulfonyl]-4-bromo-1H-pyrrole-2-carboxylic acid, methyl ester;

X-[((4-methoxy-6-methyl-1,3,5-triazin-2-yl)aminocarbonyl)aminosulfonyl]-1H-pyrrole-2-carboxylic acid, methyl ester; (X indicates mixtures of 4- and 5-substituents); and 4-bromo-5-[((4,6-dimethylpyrimidin-2-yl)aminocarbonyl)aminosulfonyl]-1-methyl-1H-pyrrole-2-carboxylic acid, ethyl ester.

DETAILED DESCRIPTION OF THE INVENTION

Methods A and B

Two general methods (A and B) for the preparation of the compounds of this invention are illustrated by the following equation:

$$R_9R_{10}NH + ClSO_2NCO \xrightarrow{\text{Step I}} ClSO_2NHC(O)N(R_9)R_{10} +$$

III

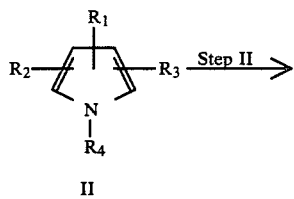

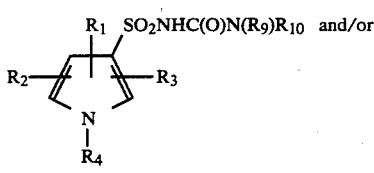

Ia

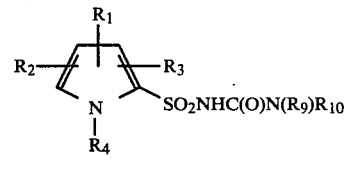

Ib

In Method A, Step I may be carried out at temperatures ranging from $-80°$ to $-40°$ C. Step II may be carried out at temperatures ranging from $-80°$ to ambient and optionally in the presence of a Friedel-Crafts catalyst. Method A is preferred for the preparation of compounds of the invention in which $R_1$ is H or alkyl and $R_4$ is other than substituted phenyl or $C(O)R_6$. In general, the conditions of Method A are usually insufficient to effect conversion of pyrroles II in which $R_1$ is other than alkyl or H or in which $R_4$ is substituted phenyl or $C(O)R_6$ to the compounds of the invention, Ia or Ib, in synthetically useful yields.

In Method B, Step I is carried out at temperatures ranging from $-10°$ C. to $10°$ C. Step II is performed at temperatures ranging from $-10°$ to the boiling point of the solvent employed and in the presence of equimolar Friedel-Crafts catalyst. Method B is preferred for the preparation of compounds of the invention in which $R_1$ is other than H or alkyl or in which $R_4$ is substituted phenyl or $C(O)R_6$.

Synthesis—Method A

As indicated above, compounds of this invention may be prepared by contacting a heterocyclic amine $R_9R_{10}NH$ and chlorosulfonyl isocyanate to form an intermediate compound of Formula III which is then contacted with a pyrrole of Formula II, optionally in the presence of a Friedel-Crafts catalyst, to produce herbicidal N-(substituted heterocyclic aminocarbonyl)-pyrrole sulfonamides of Formulae Ia and Ib. In some instances, isomeric products are obtained and these materials may be separated by column chromatography, preparative high pressure or medium pressure liquid chromatography or similar methods. In cases in which isomer separation cannot be carried out successfully or can be accomplished only with great difficulty, the isomeric identity of the products is sometimes uncertain and it should be understood that the compounds of this invention may include these isomeric products.

The heterocyclic amine $R_9R_{10}NH$ is suspended or dissolved in an inert organic solvent, such as dichloromethane, nitroethane, nitropropanes or tetrahydrofuran. Tetrahydrofuran or nitroethane are preferred. The reaction mixture is preferably maintained in an inert atmosphere at a temperature of $-80°$ to $-40°$ C. One equivalent of chlorosulfonyl isocyanate, either neat or, if tetrahydrofuran is not the solvent, dissolved in the corresponding solvent, is contacted with the starting material at such a rate as to maintain the reaction temperature within the preferred range. Reaction Step I proceeds rapidly and is allowed to continue for a period of 0.1 to 1 hour to insure complete formation of intermediate III. This compound is preferably not isolated, but is contacted at $-80°$ to $-40°$ with one to ten equivalents of pyrrole II, dissolved in the corresponding solvent. Use of one equivalent of pyrrole II is preferred.

Step II is optionally carried out in the presence of a Friedel-Crafts catalyst such as aluminum (III) chloride, aluminum (III) bromide, gallium (III) chloride, tin (IV) chloride, iron (III) chloride, antimony (V) chloride, antimony (V) fluoride, zinc (II) chloride, antimony (III) chloride, titanium (IV) chloride, boron (III) fluoride, sulfuric acid or hydrofluoric acid. The use of such a catalyst in Step II of the reaction is the method of choice. Preferred is aluminum (III) chloride in catalytic quantities, the exact amounts of which would be apparent to one skilled in the art. The reaction mixture is allowed to warm to ambient temperature and maintained there for a period of from 0.5 to 24 hours. The reaction is conveniently monitored by observing the disappearance of starting pyrrole II by thin layer chromatography in a suitable solvent system.

In some cases, the products of Formulae Ia and/or Ib may be isolated by partitioning the reaction mixture between dilute aqueous alkali and an organic solvent such as dichloromethane or chloroform. The products are soluble in the aqueous phase and may be precipitated from it, after separation of the layers, by the addition of an excess of an acid such as acetic acid or hydrochloric acid. If the products do not precipitate on acidification they may then be isolated by extraction into an organic solvent such as dichloromethane or ethyl acetate followed by evaporation of the solvent. This procedure is most useful in cases in which tetrahydrofuran is the reaction solvent.

When the reaction is carried out in water-immiscible solvents such as dichloromethane or nitroethane, isolation of the products may best be carried out by contacting the reaction mixture with water, followed by separation of the organic phase and further extraction of the products into an organic solvent such as dichloromethane, nitromethane, nitroethane or ethyl acetate.

After evaporation of the solvent, purification of the reaction products may be accomplished by trituration with an appropriate solvent, recrystallization or chromatography.

Synthesis—Method B

Method B is procedurally similar to Method A. For this method, suitable solvents include but are not limited to nitromethane, nitroethane, nitropropanes and dichloromethane; nitromethane is the solvent of choice. The reaction mixture is initially maintained at a temperature of −20° to 0° and Step I is preferably carried out between −10° and 10° C. Again, a reaction time of 0.1 to 1 hour is allowed for the formation of intermediate III. The compound is contacted at −10° to 10° C. with one equivalent of pyrrole II followed by an equimolar amount of Friedel-Crafts catalyst, preferably aluminum (III) chloride. The reaction mixture is allowed to warm to ambient temperatures and then, Step II of the reaction is allowed to proceed at temperatures ranging from ambient to the boiling point of the solvent for a period of from 0.5 to 24 hours. In general, the higher reaction temperatures and shorter reaction times (0.5 to 4 hours) afford the best yields in Step II.

Products Ia and/or Ib may be isolated by the procedure described in Method A for the reaction in water-immiscible solvents and purification of the resulting compounds may be accomplished in like fashion. The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. The 2-amino-1,3,5-triazines are reviewed by E. M. Smolin and L. Rapaport in "s-Triazines and Derivatives," Vol. XIII of the same series. The synthesis of triazines is also described by F. C. Schaefer, U.S. Pat. No. 3,154,547 and by K. R. Huffman and F. C. Schaefer, *J. Org. Chem.*, 28, 1812–1821 (1963). The synthesis of the bicyclic heterocyclic amines IV and V wherein $Y^1$ is as previously defined is described in the unexamined European Patent 15-683, published Sept. 17, 1980.

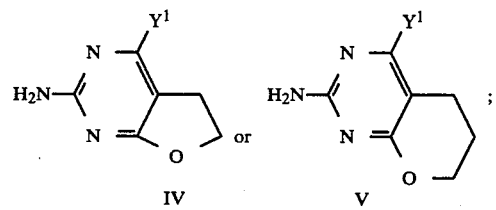

The pyrimidine intermediates of structure VI in which $Y^1$ is methyl, have been reported in the literature by E. Bisagni, et. al., *Bull. Soc. Chim. Fr.*, 803 (1969). A more efficient procedure is depicted in the equation below.

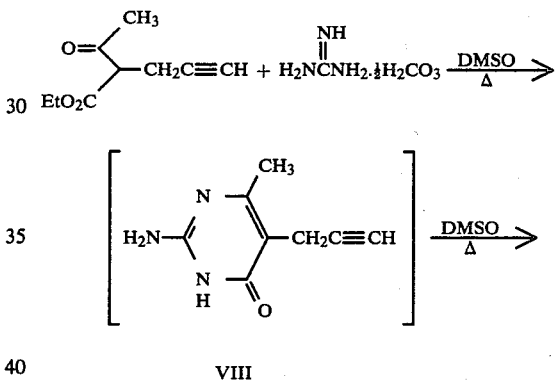

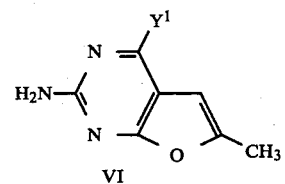

The known keto-ester precursor VII (e.g., J. F. Tinker and T. E. Whatmough, *J. Amer. Chem. Soc.*, 74, 5235 (1952)) is treated with excess guanidine carbonate in an organic solvent, preferably a polar aprotic solvent such as dimethylsulfoxide (DMSO), dimethylformamide (DMF) or N,N-dimethylacetamide, at a temperature of 80° to 200°, preferably 100° to 160°, ambient pressure and preferably under an inert atmosphere to yield both VIII and VI (where $Y^1$ is $CH_3$). The products are isolated upon dilution of the reaction mixture with, for example, acetone and water successively. Higher reaction temperatures and longer reaction times (e.g., in DMSO at 130° to 150° for 2 to 8 hours) favor the production of VI over VIII.

The pyrimidine intermediates VI in which $Y^1$ is Cl may be prepared by condensing the known ethyl 2-carboethoxy-4-pentynoate IX with guanidine carbonate in an alcohol solvent such as ethanol to give the intermediate pyrimidine X as shown below.

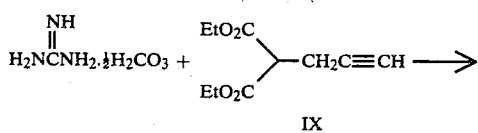

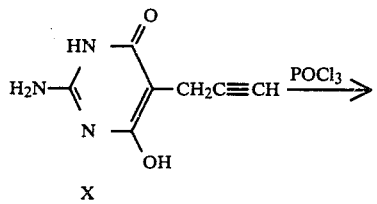

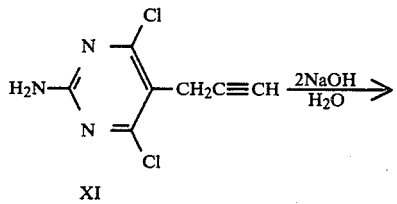

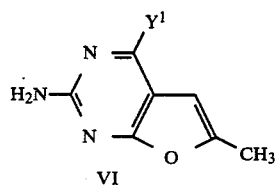

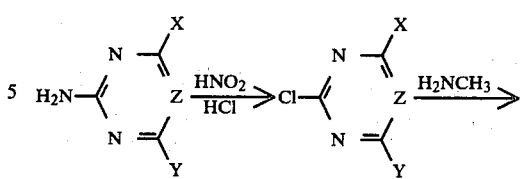

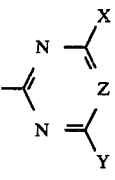

Conversion to the dichloropyrimidine XI may be accomplished by heating X in phosphorous oxychloride. The product may be isolated by removal of the phosphorous oxychloride under reduced pressure, trituration of the residue with ice-water and filtration of th solid product. Contacting the dichloropyrimidine with two equivalents of an aqueous alkali metal hydroxide, such as sodium hydroxide, yields the furopyrimidine VI in which $Y^1$ is Cl. The reaction is best carried out in the presence of a solubilizing agent which is water miscible, such as t-butanol, dioxane or tetrahydrofuran, and at temperatures of 20° to 100° or at the boiling point of the solvent mixture used. The product may be isolated by cooling the mixture or further dilution with water to effect precipitation.

Compounds of Formula VI in which $Y^1$ is $OCH_3$ or $OCH_2CH_3$ may be prepared by treatment of the corresponding compound in which $Y^1$ is Cl with sodium methoxide in boiling methanol or with sodium ethoxide in refluxing ethanol, respectively. The product is obtained on evaporation of the alcohol solution, trituration of the residue with cold water and subsequent filtration.

Compounds of Formula VI in which $Y^1$ is H may be prepared by reaction of the corresponding compound in which $Y^1$ is Cl with a reducing agent such as zinc dust in acetic acid or p-toluenesulfonylhydrazide, the latter by a procedure similar to that described by Albert and Royer, *J. Chem. Soc.*, 1148 (1949).

The aminoheterocyclic intermediates of $R_9R_{10}NH$ in which $R_9$ is $CH_3$ may be prepared by the following procedure, or by obvious modifications:

A solution of the amine XII in concentrated hydrochloric acid is treated with an aqueous sodium nitrite solution and the chloro compound XIII is isolated in the usual manner by filtration of the acidic solution (see for example, Bee and Rose, *J. Chem. Soc. C.*, 2051 (1966) for the case in which Z is CH and X and Y are $OCH_3$). Displacement of the chlorine may be accomplished by heating with an excess of methylamine in water to obtain the methylamino heterocycle XIV.

N-Methoxyamino heterocycles can be prepared by procedures reported in the literature [see, for example, Belgian Patent 618,563 and J. T. Shaw, et al., *J. Org. Chem.*, 27, 4054 (1962)] and illustrated below:

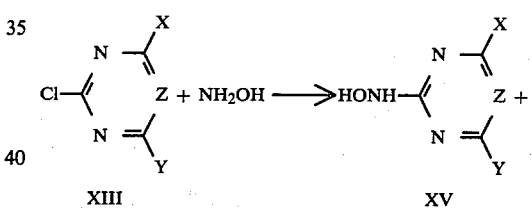

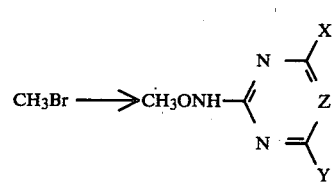

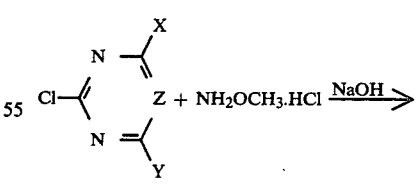

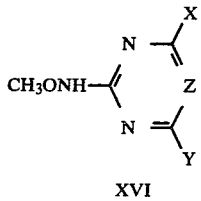

Chloro compound XIII is reacted with hydroxylamine to form derivative XV which may be alkylated with methyl bromide to afford the N-methoxy heterocyclic amine XVI. This compound may alternatively be prepared in one step by treatment of XIII and O-methyl hydroxylamine hydrochloride with an alkali metal hydroxide such as sodium hydroxide.

The pyrroles required as starting materials for this invention are represented by the generalized structure II where $R_1$, $R_2$, $R_3$ and $R_4$ are as previously defined.

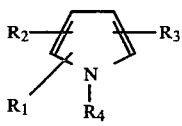

II

The synthesis of pyrroles has been extensively reviewed; e.g., by R. Alan Jones and G. P. Bean, "The Chemistry of Pyrroles", Academic Press, London (1977); by J. M. Patterson, *Synthesis*, 281-304 (1976); and by A. Gossauer, "Die Chemie der Pyrrole", Springer-Verlag, West Berlin (1974). These articles are herein incorporated by reference.

The preparation of a wide variety of alkyl substituted pyrroles by numerous routes has been reported in the literature and appropriate methods for this synthesis of pyrroles of Formula II wherein $R_1$ is H or $C_1$-$C_4$ alkyl, $R_2$ is H or $C_1$-$C_4$ alkyl, $R_3$ is H or $C_1$-$C_4$ alkyl and $R_4$ is H, $C_1$-$C_4$ alkyl, $C_5$-$C_6$ cycloalkyl or phenyl substituted by $NO_2$ or Cl would be, from the above, apparent to one skilled in the art.

For starting pyrroles in which $R_1$ is $C(O)R_5$, CN, $NO_2$ or $SO_2R_{11}$ and $R_3$ is other than Cl or Br, the accessability of the fourteen different generalized pyrrole substitution patterns shown below is required for this invention. In these structures, the values of $R_2$ and $R_3$ have been restricted to H or $CH_3$. The methods described for the synthesis of these methyl substituted compounds are, however, applicable to the preparation of the higher alkyl homologs as well.

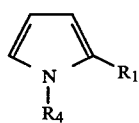

IIa

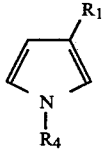

IIb

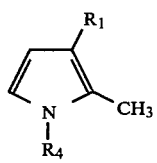

IIc

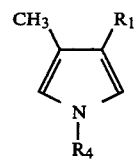

IId

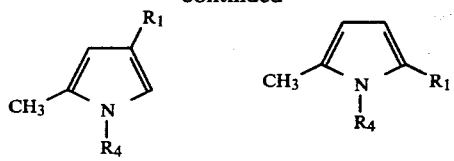

IIe IIf

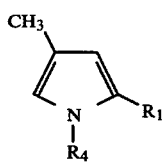

IIg

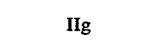

IIh

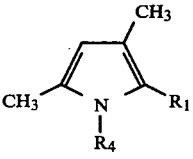

IIi

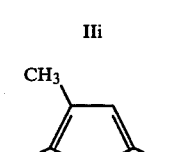

IIj

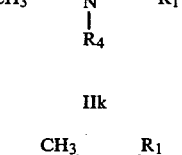

IIk  IIl

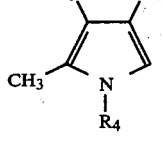

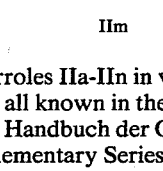

IIm

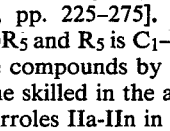

IIn

Pyrroles IIa-IIn in which $R_1$ is $CO_2CH_2CH_3$ and $R_4$ is H are all known in the literature [see for example, "Beilsteins Handbuch der Organischen Chemie", Volume 22, Supplementary Series III/IV, Springer-Verlag (Berlin), 1979, pp. 225-275]. The other pyrrole esters ($R_1$ is $C(O)R_5$ and $R_5$ is $C_1$-$C_4$ alkoxy) may be prepared from these compounds by methods which would be known to one skilled in the art.

Pyrroles IIa-IIn in which $R_1$ is CN or $C(O)CH_3$ and $R_4$ is H may also be found in the literature [see for example, "Beilstein's Handbuch der Organischen Chemie", Volume 22, Supplementary Series I-IV, System Number 3181, Springer-Verlag (Berlin); P. E. Sonnet and J. C. Moser, *J. Agr. Food Chem.*, 20, (6) 1191-4 (1972); P. Pfaffli and C. Tamm, *Helv. Chim. Acta.*, 52 (7) 1911-20 (1969); L. F. Elsom and R. A. Jones, *J. Chem. Soc. B.*, (1) 79-81 (1970) and references therein; A. M. van Leusen, et. al., *Tetrahedron Lett.*, 5337 (1972); J. W. Ducker and M. J. Gunter, *Aust. J. Chem.*, 26 (7) 1551-69 (1973)]. The methods used for the preparation of these compounds in which $R_1$ was $C(O)CH_3$ can be readily applied to the synthesis of similar systems in which $R_1$ is $C(O)R_5$ and $R_5$ is $C_1$–$C_4$ alkyl.

Pyrroles of structures IIa, IIb, IIc, IIf and IIn in which $R_1$ is $NO_2$ and $R_4$ is H are known in the literature [K. J. Morgan and D. P. Morrey, *Tetrahedron* 22, 57–62 (1966); P. E. Sonnet, *J. Het. Chem.*, 7 (2) 399–400 (1970); T. A. Melent'eva, et. al., *Zh. Obshch. Khim.*, 41, 179 (1971); T. A. Melent'eva, et. al., ibid, 42 2274 (1972)]. Nitration of 3-methyl pyrrole with nitric acid in acetic anhydride at low temperatures affords a mixture of pyrroles IIg and IIh. Similarly, reaction with 2,3-dimethylpyrrole affords a mixture of IIk and IIm. These isomeric products may be separated by chromatography to afford the desired systems. Nitration of 2,5-dimethylpyrrole, 3,4-dimethylpyrrole and 2,4-dimethylpyrrole under the conditions described above affords III, IIj and IIi respectively. Nitration of the known diethyl ester of 5-methyl-2,4-pyrroledicarboxylic acid, followed by alkaline hydrolysis to the diacid and decarboxylation in refluxing 2-aminoethanol or in quinoline with copper chromite at 180° produces pyrrole IIe. A similar sequence beginning with the known diethyl ester of 3-methyl-2,5-pyrroledicarboxylic acid gives access to IId.

The preparation of pyrrole IIa in which $R_1$ is $SO_2CH_3$ and $R_4$ is H is described by R. K. Olsen and H. R. Snyder, *J. Org. Chem.*, 28, 3050 (1963). Procedures described in this reference, by R. L. N. Harris, *Aust. J. Chem.*, 23, 1199–207 (1970); R. L. N. Harris and S. Beveridge, ibid, 24, 1229–36 (1971) and by R. L. N. Harris, ibid, 25, 985–91 (1972) are useful for the synthesis of alkylsulfonyl pyrroles. Contacting of the known pyrrole dicarboxylic acid esters XVIIa-c

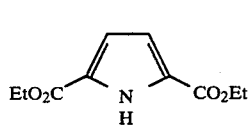

XVIIa

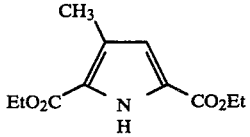

XVIIb

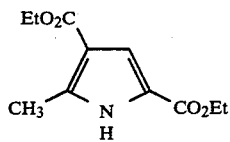

XVIIc

["Beilstein's Handbuch der Organischen Chemie", Volume 22, Supplementary Series III/IV, Springer-Verlag (Berlin) 1979, pp. 1543–1561] either with thiourea in the presence of iodine and potassium iodide or with a thiocyanogen halide followed by alkaline hydrolysis to the thiol salt, alkylation with an appropriate alkyl halide, oxidation to the sulfone with 30% hydrogen peroxide in acetic acid, ester hydrolysis and decarboxylation as before affords IIb, IId and IIe, (where $R_1$ is $SO_2R_{11}$ and $R_4$ is H), respectively. A similar reaction sequence starting with the mono-carboxylic acid esters IIh, IIg, IIf and IIk ($R_1$ is $CO_2CH_2CH_3$ and $R_4$ is H) gives access to pyrroles IIg, IIh, IIc and IIm (where $R_1$ is $SO_2R_{11}$ and $R_4$ is H), respectively. The remaining pyrrole sulfones II may be prepared from the corresponding alkyl pyrroles ($R_1$ is H and $R_4$ is H) by reaction with thiourea or a thiocyanogen halide, hydrolysis, alkylation and oxidation as above.

Pyrroles IIa, IIf, IIi, IIk and III are starting materials when $R_1$ is $COCCl_3$. When $R_1$ is $COCCl_3$ and $R_4$ is H, pyrroles IIa, IIi and III are known in the literature [J. W. Harbuck and H. Rapaport, *J. Org. Chem.*, 37, 3618–22 (1972); A. Treibs and F. -H. Kreuzer, *Ann. Chim.*, 721, 105–15 (1969)]. Pyrroles IIf and IIk ($R_1$ is $COCCl_3$ and $R_4$ is H) may be prepared in like fashion by treatment of the corresponding alkyl pyrroles ($R_1$ is H) with trichloroacetyl chloride in chloroform, optionally in the presence of a base such as 2,6-lutidine or potassium carbonate.

The halopyrroles required as starting materials may be represented by structures XVIIIa-b in which $R_3$ is Cl or Br and $R_1$ is $NO_2$, CN, $SO_2R_{11}$ or $C(O)R_5$.

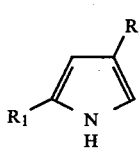 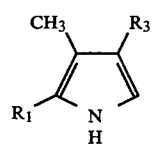

XVIIIa  XVIIIb

Again, $R_2$ has been illustrated by H and $CH_3$ and $R_4$ by H for simplicity and the methods described for the preparation of these compounds may be applied to the synthesis of higher alkyl homologs of $R_2$. Pyrroles of structure XVIIIa in which $R_1$ is $NO_2$ and $R_3$ is Br, $R_1$ is $C(O)CH_3$ and $R_3$ is Cl or Br, and in which $R_1$ is $CO_2CH_3$ and $R_3$ is Cl or Br are known in the literature [P. E. Sonnet, *J. Het. Chem.* 7, 1101 (1970); P. E. Sonnet and J. C. Moser, *Env. Ent.*, 2 (5) 851–4 (1973); and P. Hodge and R. W. Richards, *J. Chem. Soc.*, 459–470 (1965)]. The remaining halopyrroles may be prepared by treatment of pyrroles XVIII ($R_3$=H) with bromine, chlorine or sulfuryl chloride. In some instances, mixtures of the 4- and 5-halopyrroles may be obtained and can be separated by chromatography. The preferred method for the preparation of structures XVIIIa in which $R_1$ is $C(O)R_5$ ($R_5$ is alkoxy) involves the use of compound XIX as an intermediate [P. Belanger, *Tetrahedron Lett.*, 2505–2508 (1979)].

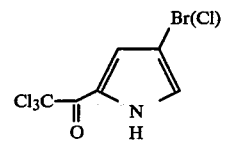

XIX

Compounds XIX may be converted first to the carboxylic acids and then to the corresponding acid chlorides and reacted with alkoxides to afford the desired products. For primary alkoxides this reaction may be carried out directly with pyrroles XIX in the corresponding alcohol or an inert aprotic solvent.

The preceeding pyrroles in which $R_4$ is H may be converted to the corresponding compounds in which $R_4$ is alkyl, cycloalkyl, benzyl, cyanoethyl or $C(O)R_6$ by formation of the alkali metal salt of the pyrrole nitrogen, preferably the potassium salt, and treatment with an appropriate reagent in an inert solvent such as benzene, toluene, tetrahydrofuran or dimethylformamide. The alkyl, cycloalkyl and benzyl derivatives may also be efficiently prepared by the phase transfer method of W. C. Guida and D. J. Mathre, *J. Org. Chem.*, 45 3172 (1980). Reaction of the appropriate N-pyrrole alkali metal salts with acrylonitrile, acyl halides, alkylhaloformates or dialkylcarbamoyl halides should afford the corresponding pyrroles in which $R_4$ is cyanoethyl and $C(O)R_6$ where $R_6$ is alkyl, alkoxy and amino, respectively. Such conversions are well known in the literature and suitable conditions would be obvious to one skilled in the art.

Compounds Ia and Ib of the invention with some values of $R_1$ may be used in certain instances to conveniently prepare the corresponding systems with different values of $R_1$. Compounds of structure Ia, in which $R_1$ is $C(O)CCl_3$ (XX) are especially useful as intermediates and may be readily converted to the corresponding carboxylic acids or esters. Treatment of XX with two equivalents of an aqueous alkali metal alkoxide, followed by precipitation of the product with dilute aqueous acid and filtration affords the corresponding carboxylic acid XXI. Reaction of XX with two equivalents of primary alkoxides in the corresponding alcoholic solvent or in an aprotic solvent such as acetonitrile or tetrahydrofuran followed by dilution with water and acidification gives rise to esters of Formula XXII in which $R_5$ is $OCH_3$, $OCH_2CH_3$, $O(CH_2)_2CH_3$, $OCH_2CH(CH_3)_2$ or $O(CH_2)_3CH_3$.

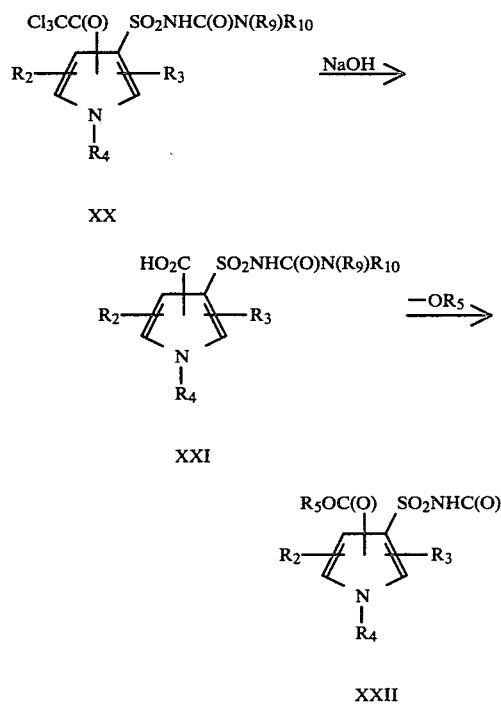

Methyl esters of Formulae Ia or Ib ($R_1$ is $C(O)R_5$ and $R_5$ is $OCH_3$) may be converted to the corresponding acids or to secondary carboxylic esters by methods disclosed in unexamined European Pat. No. 7687, filed Feb. 6, 1980.

The compounds of the invention and their preparation are further illustrated by the following examples. In the following examples, unless otherwise indicated, all parts are by weight and all temperatures in °C.

EXAMPLE 1

Preparation of N-[(4,6-dimethylpyrimidin-2-yl)aminocarbonyl]-2,5-dimethyl-1H-pyrrole-3-sulfonamide.

To a mechanically stirred suspension of 12.3 g (0.1 mole) of 2-amino-4,6-dimethylpyrimidine in 200 ml of dry dichloromethane maintained at 0° to 5° C. under a nitrogen atmosphere was added dropwise over 30 minutes a solution of 9.2 ml (0.1 mole) of chlorosulfonyl isocyanate in 50 ml of ice-cold dichloromethane. After 30 minutes at 0° to 5° C. the resulting yellow solution was treated dropwise over 15 minutes with 20 ml (0.197 mole) of 2,5-dimethylpyrrole. This mixture was stirred 30 minutes at 0° to 5° C. and allowed to stand overnight at room temperature.

The dichloromethane solution was decanted and the resulting reddish solid dissolved in a mixture of 50 ml methanol and 600 ml of 1 N sodium hydroxide solution, acidified with 10% HCl and extracted with 4 portions of ethyl acetate. The ethyl acetate was evaporated in vacuo to afford a brown solid which was dissolved in 50 ml methanol and 300 ml of dilute NaOH solution. The aqueous solution was washed with 2 portions of $CH_2Cl_2$, acidified with glacial acetic acid and extracted with 2 portions of $CH_2Cl_2$. The latter $CH_2Cl_2$ solutions were evaporated to afford the crude product which was purified by fractional crystallization from 20% acetone in $CH_2Cl_2$ to afford a white solid, m.p. 220°–222°. Mass spectral analysis

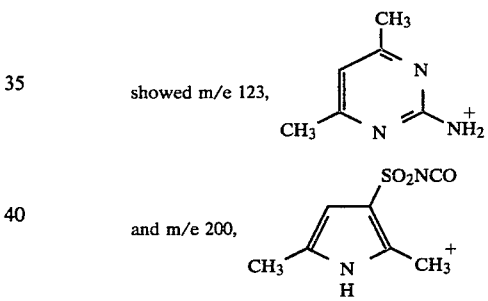

showed m/e 123, and m/e 200,

Anal. Calcd. for $C_{13}H_{17}N_5O_3S$: C, 48.3; H, 5.3; N, 21.7; S, 9.9. Found: C, 48.4; H, 5.4; N, 22.0; S, 9.8.

EXAMPLE 2

Preparation of N-[(4,6-dimethylpyrimidin-2-yl)aminocarbonyl]-1H-pyrrole-2-sulfonamide.

Method A

To a mechanically stirred mixture of 12.3 g (0.1 mole) of 2-amino-4,6-dimethylpyrimidine in 200 ml dry tetrahyrofuran at 0° to 5° C. under a nitrogen atmosphere was added dropwise via syringe 9.2 ml (0.1 mole) of chlorosulfonyl isocyanate at such a rate to maintain the temperature below 5° C. After 10 minutes at 0° the solution was treated with 14.0 ml (0.2 mole) of pyrrole, stirred 15 minutes at 0° then allowed to stand at room temperature overnight.

The resulting gummy slurry was diluted with 50 ml methanol and 100 ml dilute NaOH solution. After 30 minutes, this solution was washed with 2 portions of $CH_2Cl_2$ and acidified with glacial acetic acid. The precipitate was collected and washed with water to afford 9.5 g (32%) of crude product. A pure sample was obtained by separation from the minor pyrrole-3-sulfonamide using high pressure liquid chromatography to give a white solid, m.p. 226°-227° (d). Mass spectral analysis showed m/e 123,

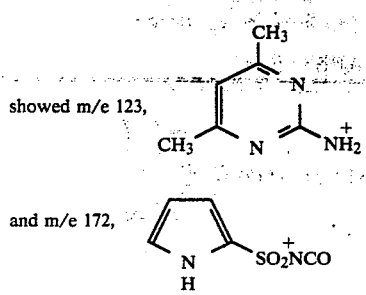

and m/e 172,

Anal. Calcd. for $C_{11}H_{13}N_5O_3S$: C, 44.7; H, 4.4; N, 23.7. Found: C, 45.2; H, 4.6; N, 24.0.

Preferred Method B

To a stirred mixture of 7.1 g (0.057 mole) of 2-amino-4,6-dimethylpyrimidine in 35 ml of dry tetrahydrofuran at −78° C. under a nitrogen atmosphere was added dropwise via syringe 5.0 ml (0.057 mole) of chlorosulfonyl isocyanate at such a rate to maintain the temperature below −50° C. After 30 minutes at −70° C., this solution was added dropwise over 10 minutes to a mixture of 8.0 ml (0.115 mole) of pyrrole, 0.3-0.5 g of aluminum (III) chloride and 35 ml dry THF at −78° C. under a nitrogen atmosphere. The reaction mixture was allowed to warm gradually to room temperature and allowed to stand at room temperature overnight.

The reaction mixture was diluted with 150 ml $H_2O$ and made alkaline by addition of 50% NaOH solution. This slurry was filtered and the filtrate washed with 2 portions $CH_2Cl_2$ and acidified with glacial acetic acid. The precipitate was collected, washed well with water and dried to afford 11.5 g (68%) of crude product as above.

EXAMPLE 3

Preparation of 1-(2-cyanoethyl)-N-[(4,6-dimethylpyrimidin-2-yl)aminocarbonyl]-1H-pyrrole-2-sulfonamide.

To a stirred suspension of 2.59 g (0.021 mole) of 2-amino-4,6-dimethylpyrimidine in 80 ml dry tetrahydrofuran at −70° C. under nitrogen was added dropwise via syringe 2.0 ml (0.023 mole) of chlorosulfonyl isocyanate at such a rate to maintain the temperature of the reaction mixture below −55° C. The resulting solution was stirred 0.5 hour at −70°, then treated dropwise with a solution of 2.4 ml (0.021 mol) of N-(2-cyanoethyl)pyrole in 10 ml dry THF. A catalytic amount (approximately 0.2 to 0.3 gm) of aluminum (III) chloride was added and the reaction mixture allowed to warm to ambient temperatures and stirred for an additional 18 hours. The reaction mixture was poured into 300 ml of $H_2O$ and extracted with three portions of dichloromethane. The organic solutions were washed with water, dried over $MgSO_4$ and evaporated. Trituration with a small volume of $CH_2Cl_2$ afforded 1.2 g of the desired product as a white microcrystalline solid, m.p. 158°-159° C. The infrared spectrum of the product included absorptions at 3250 and 3110 (NH), 2240 (C≡N), 1685 (C=O), 1350 and 1160 cm$^{-1}$ ($SO_2$).

EXAMPLE 4

Preparation of 4-[((4,6-dimethylpyrimidin-2-yl)aminocarbonyl)aminosulfonyl]-1H-pyrrole-2-carboxylic acid, methyl ester.

To a stirred suspension of 2.58 g (0.021 mol) of 2-amino-4,6-dimethylpyrimidine in 75 ml dry nitromethane at −10° was added dropwise, via syringe, under nitrogen, 2.0 ml (0.023 mol) of chlorolsulfonyl isocyanate at such a rate to maintain the temperature below 0°. The resulting clear solution was stirred 0.5 hour at −5° to −10°, then treated dropwise with a solution of 2.29 g (0.021 mole) of methyl pyrrole-2-carboxylate in 25 ml dry nitromethane. Upon completion of the addition, 2.95 gm (0.022 mole) of aluminum (III) chloride was added in one portion. The reaction mixture was heated at reflux for 2 hours, then allowed to stand overnight at ambient temperatures. The mixture was poured into 300 ml $H_2O$ and the two phase system extracted with three portions of $CH_2Cl_2$. The organic solutions were washed with water, dried over $MgSO_4$ and evaporated to a tan foam which was triturated with minimal $CH_2Cl_2$ to afford the product as a white solid, m.p. 202°-204°.

Anal. Calcd. for $C_{13}H_{15}N_5O_5S$: C, 44.19; H, 4.28; N, 19.82; S, 9.07. Found: C, 42.4; H, 4.1; N, 19.4; S, 8.95.

EXAMPLE 5

Preparation of the methyl ester of 4-bromo-5-[((4,6-dimethylpyrimidin-2-yl)aminocarbonyl)aminosulfonyl]-1H-pyrrole-2-carboxylic acid.

To a stirred suspension of 2.58 g (0.021 mole) of 2-amino-4,6-dimethylpyrimidine in 75 ml dry nitromethane at −10° was added dropwise, via syringe, under nitrogen, 2.0 ml (0.023 mole) of chlorosulfonyl isocyanate at such a rate to maintain the temperature below 0°. The resulting clear solution was stirred 0.5 hour at −5° to −10°, then treated dropwise with a solution of 4.28 g (0.021 mol) of methyl 4-bromopyrrole-2-carboxylate in 25 ml dry $CH_3NO_2$. Upon completion of the addition, 2.95 g (0.022 mol) of aluminum (III) chloride was added in one portion and the reaction mixture heated at reflux for 3 hours. Workup as in Example 4 and chloroform trituration afforded 4.51 g (50%) of product as a white, microcrystalline solid, m.p. 126°-128°. The infrared spectrum of the product included resonances at 3160 (NH), 1710 (C=O), 1340 and 1160 ($SO_2$)cm$^{-1}$.

EXAMPLE 6

Preparation of N-[(4,6-dimethylpyrimidin-2-yl)aminocarbonyl]-5-trichloroacetyl-1H-pyrrole-2-sulfonamide.

To a stirred suspension of 2.59 g (0.021 mol) of 2-amino-4,6-dimethylpyrimidine in 60 ml dry $CH_3NO_2$ at −10° was added dropwise, via syringe, under nitrogen, 2.0 ml (0.023 mole) of chlorosulfonyl isocyanate at such a rate to maintain the temperature below 5°. The resulting clear solution was stirred 0.5 hour at −5°, then treated dropwise with a solution of 4.46 g (0.021 mole) of 2-trichloroacetyl-1H-pyrrole in 30 ml dry $CH_3NO_2$. Upon completion of the addition, 2.95 g (0.022 mole) of aluminum (III) chloride was added in one portion and the reaction mixture stirred 1.5 hour at ambient temperatures followed by 0.5 hour under reflux. The cool solution was poured into $H_2O$, diluted with $CH_2Cl_2$ and the layers separated. A precipitate was present in the aqueous layer and was collected by filtration and washed well with water. The organic solution was washed with $H_2O$, dried over $MgSO_4$, evaporated and triturated with CH₂Cl₂ to afford a second crop of product. Total yield of product was 2.45 g of a tan solid, m.p. 215°-218° (d). The infrared spectrum of the product included absorptions at 3230 (NH), 1692 (C=O), 1340 and 1160 cm⁻¹ (SO₂).

By using methods described generally above and illustrated in Examples 1-6, compounds as shown in the following tables can similarly be prepared. These tables are not meant to be all inclusive but only illustrative of the breadth of the invention.

TABLE I

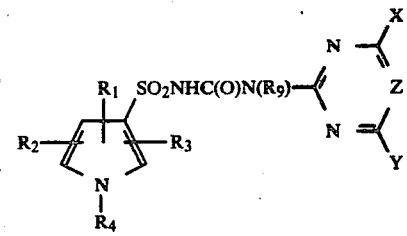

| R₁ | R₂ | R₃ | R₄ | R₉ | X | Y | Z | m.p. (°C.) |
|---|---|---|---|---|---|---|---|---|
| H | H | H | H | H | CH₃ | CH₃ | CH | |
| H | H | H | H | H | OCH₃ | OCH₃ | N | >300* |
| H | H | H | H | H | CH₃ | Cl | CCl | |
| H | H | H | H | CH₃ | CH₃ | CF₃ | CCH₃ | |
| H | H | H | H | OCH₃ | OCH₃ | OC₂H₅ | CC₂H₅ | |
| H | H | H | CH₃ | H | CH₃ | CH₃ | CH | 190-192* |
| H | H | H | CH₂C₆H₅ | H | CH₃ | CH₃ | CH | 132-140* |
| H | H | H | t-C₄H₉ | CH₃ | OCH₃ | CH₃ | CC₂H₅ | |
| H | H | H | C(O)C₃H₇ | CH₃ | OCH₃ | OC₂H₅ | N | |
| H | H | H | C(O)N(Me)₂ | H | OCH₃ | H | N | |
| H | H | H | p-NO₂C₆H₄ | H | OCH₃ | H | CF | |
| 5-CH₃ | H | 2-CH₃ | CO₂C₂H₅ | H | OCH₃ | H | CBr | |
| 5-C₄H₉ | H | H | COCH₃ | OCH₃ | OCH₃ | OCH₃ | CH | |
| 5-CH₃ | H | 2-CH₃ | H | H | CH₃ | CH₃ | CH | 220-222 |
| 5-CH₃ | 2-CH₃ | H | H | H | CH₃ | OCH₃ | CH | 127-131 |
| 5-CH₃ | 2-CH₃ | H | H | H | OCH₃ | OCH₃ | N | 209-211 |
| 5-CH₃ | 2-CH₃ | H | H | H | OCH₃ | CH₃ | N | 205-207 |
| 5-CH₃ | 2-CH₃ | H | CH₃ | H | CH₃ | CH₃ | CH | 200-204 |
| 5-C₂H₅ | 2-C₂H₅ | H | cyclohexyl | CH₃ | CH₃ | Cl | C(CH₂)₂Cl | |
| 5-CH₃ | 2-CH₃ | H | O—ClC₆H₄ | H | CH₃ | Cl | CCH₃ | |
| 5-CH₃ | 2-CH₃ | H | (CH₂)₂CN | OCH₃ | CH₃ | CH₂OC₂H₅ | CH₃ | |
| 4-NO₂ | 2-CH₃ | 5-CH₃ | H | CH₃ | OCH₃ | CH₂OC₂H₅ | N | |
| 2-NO₂ | 5-C₄H₉ | 4-CH₃ | H | OCH₃ | OCH₃ | Cl | CCH₃ | |
| 5-CN | H | H | C₃H₇ | CH₃ | CH₃ | OCH₃ | CCl | |
| 2-CN | C₂H₅ | C₂H₅ | H | H | CH₃ | OCH₂CF₃ | N | |
| 4-CN | CH₃ | CH₃ | H | H | CH₃ | OC₂H₅ | | |
| 5-COCCl₃ | H | H | H | H | CH₃ | CH₃ | CH | 215-218 |
| 5-COCCl₃ | H | H | CH₃ | H | CH₃ | CH₃ | CH | 203-205 |
| 4-COCCl₃ | 5-C₃H₇ | 2-C₃H₇ | H | CH₃ | CH₃ | OCH₃ | N | |
| 5-SO₂CH₃ | H | H | CH₃ | H | CH₃ | H | N | |
| 5-SO₂CH₃ | 2-C₃H₇ | H | H | H | CH₃ | H | CH | |
| 2-SO₂C₃H₇ | 4-C₂H₅ | 5-CH₃ | H | H | CH₃ | Cl | CH | |
| 4-SO₂C₄H₉ | 5-CH₃ | 2-CH₃ | H | H | CH₃ | Cl | CCH₃ | |
| 5-COCH₃ | H | H | C₃H₇ | H | CH₃ | CH₃ | C(CH₂)₂Cl | |
| 5-COC₄H₉ | H | H | H | OCH₃ | CH₃ | CH₃ | CH | |
| 2-COCH₃ | 4-C₄H₉ | 5-CH₃ | H | OCH₃ | CH₃ | CH₃ | CCl | |
| 5-CO₂CH₃ | H | H | H | H | CH₃ | OCH₃ | N | 110(d)* |
| 5-CO₂CH₃ | H | H | H | H | OCH₃ | OCH₃ | N | 184-188 |
| 5-CO₂CH₃ | H | H | H | H | CH₃ | CH₃ | CH | 202-204 |
| 5-CO₂CH₃ | H | H | CH₃ | H | CH₃ | CH₃ | CH | 91-96* |
| 4-CO₂C₂H₅ | 2-CH₃ | 5-CH₃ | H | H | CH₃ | CH₃ | CH | 223-225 |
| 4-CO₂t-C₄H₉ | H | H | H | H | OCH₃ | OC₂H₅ | CCl | |
| 5-CO₂H | H | H | H | H | CH₃ | CH₃ | CH | 198-200 |
| 5-CO₂H | H | H | n-C₄H₉ | CH₃ | OCH₃ | Cl | CH | |
| 4-CO₂H | 5-CH₃ | 2-CH₃ | H | H | OCH₃ | OC₂H₅ | CCH₃ | |
| 2-CO₂H | 5-C₂H₅ | 4-C₂H₅ | H | H | OCH₃ | Cl | N | |

*m.p. is for an isomeric product mixture consisting of this compound and the corresponding entry in Table V.

TABLE II

| R1 | R2 | R3 | R4 | R9 | Y1 | m.p. (°C.) |
|---|---|---|---|---|---|---|
| H | H | H | H | H | CH3 | |
| H | H | H | H | H | Cl | |
| H | H | H | H | H | OC2H5 | |
| H | H | H | H | CH3 | Cl | |
| H | H | H | H | OCH3 | OCH3 | |
| H | H | H | C2H5 | H | OCH3 | |
| H | H | H | (CH2)2CN | H | CH3 | |
| H | H | H | t-C4H9 | CH3 | CH3 | |
| H | H | H | n-Cl—C6H4 | H | CH3 | |
| H | H | H | CO2C2H5 | CH3 | H | |
| 5-CH3 | H | 2-CH3 | COC4H9 | H | CH3 | |
| 5-CH3 | 2-CH3 | H | COCH3 | H | H | |
| 5-CH3 | H | 2-CH3 | CONMe2 | H | CH3 | |
| 5-C2H5 | 2-C2H5 | H | p-NO2C6H4 | H | CH3 | |
| 5-CH3 | 2-CH3 | H | CH3 | CH3 | CH3 | |
| 5-C4H9 | 2-C4H9 | H | H | OCH3 | OCH3 | |
| CH3 | CH3 | CH3 | H | OCH3 | OCH3 | |
| 5-COCCl3 | H | H | CH3 | CH3 | OCH3 | |
| 5-COCCl3 | H | 5-C2H5 | H | H | Cl | |
| 4-COCCl3 | i-C3H7 | i-C3H7 | H | H | CH3 | |
| 2-NO2 | 5-CH3 | 5-i-C4H9 | H | H | CH3 | |
| 5-CN | H | H | CH3 | H | CH3 | |
| 2-CN | CH3 | CH3 | CH2C6H5 | H | Cl | |
| 4-CN | C2H5 | C2H5 | H | CH3 | OCH3 | |
| 5-CO2CH3 | H | H | H | CH3 | OCH3 | |
| 5-CO2C3H7 | H | H | C2H5 | OCH3 | CH3 | |
| 4-CO2C2H5 | 5-CH3 | 2-CH3 | t-C4H9 | H | CH3 | |
| 5-COCH3 | 4-CH3 | H | H | H | CH3 | |
| 5-COC4H9 | H | H | H | H | CH3 | |
| 2-COCH3 | 5-CH3 | 4-C3H7 | CH3 | CH3 | Cl | |
| 5-SO2CH3 | H | H | —⟨S⟩ | H | H | |
| 5-SO2C3H7 | H | 2-CH3 | H | CH3 | OC2H5 | |
| 4-SO2CH3 | 2-C2H5 | 5-C2H5 | i-C3H7 | H | CH3 | |
| 4-CO2H | C2H5 | C2H5 | H | OCH3 | H | |
| 5-CO2H | H | H | C3H7 | H | CH3 | |

TABLE III

| R1 | R2 | R3 | R4 | R9 | Y1 | m.p. (°C.) |
|---|---|---|---|---|---|---|
| H | H | H | H | H | CH3 | |
| H | H | H | H | H | Cl | |
| H | H | H | H | H | OC2H5 | |
| H | H | H | H | CH3 | Cl | |
| H | H | H | H | OCH3 | OCH3 | |
| H | H | H | C2H5 | H | OCH3 | |
| H | H | H | (CH2)2CN | H | CH3 | |
| H | H | H | t-C4H9 | CH3 | CH3 | |
| H | H | H | n-Cl—C6H4 | H | CH3 | |
| H | H | H | CO2C2H5 | CH3 | H | |
| 5-CH3 | H | 2-CH3 | COC4H9 | H | CH3 | |
| 5-CH3 | 2-CH3 | H | COCH3 | H | H | |

TABLE III-continued

[Structure: Pyrrole with R1, R2, R3, R4 substituents linked via SO2NHC(O)N(R9) to a pyrimidine with Y1 substituent fused to an oxygen-containing ring]

| R1 | R2 | R3 | R4 | R9 | Y1 | m.p. (°C.) |
|---|---|---|---|---|---|---|
| 5-CH3 | H | 2-CH3 | CONMe2 | H | CH3 | |
| 5-C2H5 | 2-C2H5 | H | p-NO2C6H4 | H | CH3 | |
| 5-CH3 | 2-CH3 | H | CH3 | CH3 | CH3 | |
| 5-C4H9 | 2-C4H9 | H | H | OCH3 | OCH3 | |
| CH3 | CH3 | CH3 | H | OCH3 | OCH3 | |
| 5-COCCl3 | H | H | CH3 | CH3 | OCH3 | |
| 5-COCCl3 | H | 5-C2H5 | H | H | Cl | |
| 4-COCCl3 | i-C3H7 | i-C3H7 | H | H | CH3 | |
| 2-NO2 | 5-CH3 | 5-i-C4H9 | H | H | CH3 | |
| 5-CN | H | H | CH3 | H | CH3 | |
| 2-CN | CH3 | CH3 | CH2C6H5 | H | Cl | |
| 4-CN | C2H5 | C2H5 | H | CH3 | OCH3 | |
| 5-CO2CH3 | H | H | H | CH3 | OCH3 | |
| 5-CO2C3H7 | H | H | C2H5 | OCH3 | CH3 | |
| 4-CO2C2H5 | 5-CH3 | 2-CH3 | t-C4H9 | H | CH3 | |
| 5-COCH3 | 4-CH3 | H | H | H | CH3 | |
| 5-COC4H9 | H | H | H | H | CH3 | |
| 2-COCH3 | 5-CH3 | 4-C3H7 | CH3 | CH3 | Cl | |
| 5-SO2CH3 | H | H | —⟨S⟩ (thiophene) | H | H | |
| 5-SO2C3H7 | H | 2-CH3 | H | CH3 | OC2H5 | |
| 4-SO2CH3 | 2-C2H5 | 5-C2H5 | i-C3H7 | H | CH3 | |
| 4-CO2H | C2H5 | C2H5 | H | OCH3 | H | |
| 5-CO2H | H | H | C3H7 | H | CH3 | |

TABLE IV

[Structure: Pyrrole with R1, R2, R3, R4 substituents linked via SO2NHC(O)N(R9) to a pyrimidine with Y1 substituent fused to a furan ring with CH3]

| R1 | R2 | R3 | R4 | R9 | Y1 | m.p. (°C.) |
|---|---|---|---|---|---|---|
| H | H | H | H | H | CH3 | |
| H | H | H | H | H | Cl | |
| H | H | H | H | H | OC2H5 | |
| H | H | H | H | CH3 | Cl | |
| H | H | H | H | OCH3 | OCH3 | |
| H | H | H | C2H5 | H | OCH3 | |
| H | H | H | (CH2)2CN | H | CH3 | |
| H | H | H | t-C4H9 | CH3 | CH3 | |
| H | H | H | n-Cl—C6H4 | H | CH3 | |
| H | H | H | CO2C2H5 | CH3 | H | |
| 5-CH3 | H | 2-CH3 | COC4H9 | H | CH3 | |
| 5-CH3 | 2-CH3 | H | COCH3 | H | H | |
| 5-CH3 | H | 2-CH3 | CONMe2 | H | CH3 | |
| 5-C2H5 | 2-C2H5 | H | p-NO2C6H4 | H | CH3 | |
| 5-CH3 | 2-CH3 | H | CH3 | CH3 | CH3 | |
| 5-C4H9 | 2-C4H9 | H | H | OCH3 | OCH3 | |
| CH3 | CH3 | CH3 | H | OCH3 | OCH3 | |
| 5-COCCl3 | H | H | CH3 | CH3 | OCH3 | |
| 5-COCCl3 | H | 5-C2H5 | H | H | Cl | |
| 4-COCCl3 | i-C3H7 | i-C3H7 | H | H | CH3 | |
| 2-NO2 | 5-CH3 | 5-i-C4H9 | H | H | CH3 | |
| 5-CN | H | H | CH3 | H | CH3 | |
| 2-CN | CH3 | CH3 | CH2C6H5 | H | Cl | |
| 4-CN | C2H5 | C2H5 | H | CH3 | OCH3 | |

TABLE IV-continued

| $R_1$ | $R_2$ | $R_3$ | $R_4$ | $R_9$ | $Y^1$ | m.p. (°C.) |
|---|---|---|---|---|---|---|
| 5-$CO_2CH_3$ | H | H | H | $CH_3$ | $OCH_3$ | |
| 5-$CO_2C_3H_7$ | H | H | $C_2H_5$ | $OCH_3$ | $CH_3$ | |
| 4-$CO_2C_2H_5$ | 5-$CH_3$ | 2-$CH_3$ | t-$C_4H_9$ | H | $CH_3$ | |
| 5-$COCH_3$ | 4-$CH_3$ | H | H | H | $CH_3$ | |
| 5-$COC_4H_9$ | H | H | H | H | $CH_3$ | |
| 2-$COCH_3$ | 5-$CH_3$ | 4-$C_3H_7$ | $CH_3$ | $CH_3$ | Cl | |
| 5-$SO_2CH_3$ | H | H | thienyl | H | H | |
| 5-$SO_2C_3H_7$ | H | 2-$CH_3$ | H | $CH_3$ | $OC_2H_5$ | |
| 4-$SO_2CH_3$ | 2-$C_2H_5$ | 5-$C_2H_5$ | i-$C_3H_7$ | H | $CH_3$ | |
| 4-$CO_2H$ | $C_2H_5$ | $C_2H_5$ | H | $OCH_3$ | H | |
| 5-$CO_2H$ | H | H | $C_3H_7$ | H | $CH_3$ | |

TABLE V

| $R_1$ | $R_2$ | $R_3$ | $R_4$ | $R_9$ | X | Y | Z | m.p. (°C.) |
|---|---|---|---|---|---|---|---|---|
| H | H | H | H | H | $CH_3$ | $CH_3$ | CH | 226–227 |
| H | H | H | H | H | $CH_3$ | $OCH_3$ | CH | 214–217 |
| H | H | H | H | H | $OCH_3$ | $OCH_3$ | N | >300* |
| H | H | H | H | $CH_3$ | $OCH_3$ | Cl | CCl | |
| H | H | H | H | $OCH_3$ | $OCH_3$ | $CF_3$ | $CCH_3$ | |
| H | H | H | $CH_3$ | H | $CH_3$ | $CH_3$ | CH | 190–192* |
| H | H | H | $(CH_2)_2CN$ | H | $CH_3$ | $CH_3$ | CH | 158–159 |
| H | H | H | $CH_2C_6H_5$ | H | $CH_3$ | $CH_3$ | CH | 132–140* |
| H | H | H | t-$C_4H_9$ | $CH_3$ | $OCH_3$ | $OC_2H_5$ | $CC_2H_5$ | |
| H | H | H | $C(O)C_3H_7$ | $CH_3$ | $OCH_3$ | H | N | |
| H | H | H | $C(O)NMe_2$ | H | $OCH_3$ | H | N | |
| H | H | H | p-$NO_2C_6H_4$ | H | $CH_3$ | $CH_3$ | CH | 198–204 |
| 5-$CH_3$ | H | H | $CO_2C_2H_5$ | H | $CH_3$ | $OCH_3$ | CBr | |
| 5-$C_4H_9$ | 4-$CH_3$ | H | $COCH_3$ | H | $CH_3$ | $OCH_3$ | CH | |
| 4-$CH_3$ | 5-$CH_3$ | H | H | H | $OCH_3$ | Cl | N | |
| 5-$C_4H_9$ | H | H | H | $CH_3$ | $OCH_3$ | $OCH_2CF_3$ | N | |
| H | 3-$C_2H_5$ | 4-$C_2H_5$ | p-$ClC_6H_4$ | H | $OCH_3$ | $CH_3$ | $C(CH_2)_2Cl$ | |
| H | 3-$CH_3$ | 4-$C_3H_7$ | H | $CH_3$ | $OCH_3$ | $OCH_3$ | $CC_2H_5$ | |
| $CH_3$ | $CH_3$ | $CH_3$ | H | $OCH_3$ | $OCH_3$ | $CF_3$ | CF | |
| H | 4-$CH_3$ | 5-$C_2H_5$ | cyclopentyl | H | $OCH_3$ | $CH_2OCH_3$ | CH | |
| 5-$NO_2$ | H | H | H | H | $OCH_3$ | $CH_3$ | N | 166–176* |
| 5-$NO_2$ | 3-$CH_3$ | 4-$CH_3$ | H | $OCH_3$ | $OCH_3$ | $OCH_3$ | CF | |
| 4-$NO_2$ | H | H | H | H | $CH_3$ | $CH_3$ | CH | 115–122** |
| 3-$NO_2$ | H | H | H | H | $CH_3$ | $CH_3$ | CH | 115–122** |
| 4-$NO_2$ | H | 5-$C_3H_7$ | H | $CH_3$ | $CH_3$ | $OC_2H_5$ | $CCH_3$ | |
| 5-$NO_2$ | H | 3-Br | H | H | $CH_3$ | $OCH_3$ | CH | |
| 5-$NO_2$ | H | 3-Cl | $CH_3$ | H | $CH_3$ | $OCH_3$ | N | |
| 5-CN | H | 3-Cl | H | H | $CH_3$ | $OCH_3$ | N | |
| 5-CN | 3-$CH_3$ | 4-$CH_3$ | H | $OCH_3$ | $CH_3$ | Cl | CBr | |
| 4-CN | H | H | cyclopentyl | H | $CH_3$ | $CH_3$ | N | |
| 3-CN | H | H | $(CH_2)_2CN$ | H | $CH_3$ | $CH_3$ | N | |
| 5-$SO_2CH_3$ | H | H | H | H | $CH_3$ | $OCH_3$ | CH | |

TABLE V-continued

| $R_1$ | $R_2$ | $R_3$ | $R_4$ | $R_9$ | X | Y | Z | m.p. (°C.) |
|---|---|---|---|---|---|---|---|---|
| 5-$SO_2C_3H_7$ | H | 3-Br | H | H | $CH_3$ | $OCH_3$ | CH | |
| 5-$SO_2CH_3$ | 3-$C_2H_5$ | 4-$C_2H_5$ | H | H | $OCH_3$ | $OCH_3$ | CH | |
| 4-$SO_2C_2H_5$ | H | H | $C_3H_7$ | H | $OCH_3$ | $OCH_3$ | N | |
| 4-$SO_2CH_3$ | 5-$CH_3$ | H | H | H | $OCH_3$ | Cl | CH | |
| 3-$SO_2CH_3$ | H | H | H | $OCH_3$ | $OCH_3$ | Cl | N | |
| 3-$COCH_3$ | H | 5-$CH_3$ | $CH_3$ | H | $OCH_3$ | $OC_2H_5$ | CF | |
| 3-$COC_3H_7$ | H | H | H | $CH_3$ | $OCH_3$ | $CF_3$ | $CCH_3$ | |
| 4-$COCH_3$ | 5-$CH_3$ | H | H | H | $CH_3$ | $OCH_3$ | CH | |
| 4-CO—i-$C_3H_7$ | 5-$CH_3$ | 3-$C_2H_5$ | H | H | $CH_3$ | $CH_2OC_2H_5$ | N | |
| 5-$COC_4H_9$ | H | 3-Br | ⟨cyclohexyl⟩ | $CH_3$ | $CH_3$ | $CH_2OCH_3$ | N | |
| 5-$COCH_3$ | H | 3-Cl | H | H | $CH_3$ | $CH_3$ | N | |
| 5-$COCH_3$ | H | H | $CH_3$ | H | $CH_3$ | $CH_3$ | CF | |
| 5-$CO_2C_2H_5$ | H | 3-Br | $CH_3$ | H | $CH_3$ | $CH_3$ | CH | 214–216 |
| 5-$CO_2CH_3$ | H | 3-Br | H | H | $CH_3$ | $CH_3$ | CH | 126–128 |
| 5-$CO_2CH_3$ | H | H | H | H | $CH_3$ | $OCH_3$ | N | 110(d)* |
| 5-$CO_2CH_3$ | H | H | $CH_3$ | H | $CH_3$ | $CH_3$ | CH | 91–96* |
| 5-$CO_2C_4H_9$ | 3-$C_2H_5$ | H | H | H | $OCH_3$ | Cl | CF | |
| 3-$CO_2CH_3$ | H | H | H | $CH_3$ | $OCH_3$ | $OCH_3$ | $CCl_3$ | |
| 4-$CO_2C_3H_7$ | H | 5-$C_4H_9$ | H | H | $OCH_3$ | $CH_2OCH_3$ | N | |
| 5-$CO_2H$ | H | 3-Br | H | H | $CH_3$ | $CH_3$ | CH | 139–145° |
| 5-$CO_2H$ | 3-$CH_3$ | 4-$CH_3$ | H | $OCH_3$ | $CH_3$ | $OCH_3$ | CH | |
| 3-$CO_2H$ | 4-$C_2H_5$ | 5-$C_2H_5$ | ⟨cyclopentyl⟩ | H | $CH_3$ | $OCH_3$ | CH | |
| 4-$CO_2H$ | H | H | H | $CH_3$ | $CH_3$ | $CH_3$ | CH | |

*m.p. is for an isomeric product mixture consisting of this compound and the corresponding entry in Table I.
**these compounds obtained as an isomeric mixture.

TABLE VI

| $R_1$ | $R_2$ | $R_3$ | $R_4$ | $R_9$ | $Y^1$ | m.p. (°C.) |
|---|---|---|---|---|---|---|
| H | H | H | H | H | H | |
| H | H | H | H | H | $CH_3$ | |
| H | H | H | H | H | Cl | |
| H | H | H | $CH_3$ | H | $OCH_3$ | |
| H | H | H | t-$C_4H_9$ | $CH_3$ | $OCH_2CH_3$ | |
| H | H | H | ⟨cyclohexyl⟩ | $OCH_3$ | $OCH_3$ | |
| H | H | H | $(CH_2)_2CN$ | H | $CH_3$ | |
| H | H | H | $CH_2C_6H_5$ | H | $CH_3$ | |
| H | H | H | o-$ClC_6H_4$ | $CH_3$ | $CH_3$ | |
| 5-$CH_3$ | H | H | $COCH_3$ | H | $CH_3$ | |
| 5-$C_4H_9$ | 3-$CH_3$ | H | $CONMe_2$ | H | $CH_3$ | |
| H | 3-$C_2H_5$ | H | $CO_2C_2H_5$ | H | $CH_3$ | |
| H | H | H | $COC_4H_9$ | H | $OCH_3$ | |
| 4-$CH_3$ | 5-$CH_3$ | H | H | H | $OCH_3$ | |
| 5-$C_4H_9$ | H | H | H | $CH_3$ | $CH_3$ | |
| H | 3-$C_2H_5$ | 4-$C_2H_5$ | p-$NO_2C_6H_4$ | H | $CH_3$ | |
| H | 3-$CH_3$ | 4-$C_3H_7$ | H | $CH_3$ | $CH_3$ | |
| $CH_3$ | $CH_3$ | $CH_3$ | H | $OCH_3$ | $OCH_3$ | |

TABLE VI-continued

| R₁ | R₂ | R₃ | R₄ | R₉ | Y¹ | m.p. (°C.) |
|---|---|---|---|---|---|---|
| H | 4-CH₃ | 5-C₂H₅ | cyclohexyl | H | OCH₃ | |
| 5-NO₂ | H | H | H | H | OCH₃ | |
| 5-NO₂ | 3-CH₃ | 4-CH₃ | H | OCH₃ | Cl | |
| 5-NO₂ | H | 3-Br | H | H | Cl | |
| 4-NO₂ | H | 5-C₃H₇ | H | CH₃ | Cl | |
| 3-NO₂ | H | H | H | H | H | |
| 5-CN | H | 3-Cl | H | H | H | |
| 5-CN | 3-CH₃ | 4-CH₃ | H | OCH₃ | H | |
| 4-CN | H | H | cyclopentyl | H | OC₂H₅ | |
| 3-CN | H | H | (CH₂)₂CN | H | OC₂H₅ | |
| 5-SO₂CH₃ | H | 3-Br | H | H | OC₂H₅ | |
| 5-SO₂C₃H₇ | H | H | H | H | CH₃ | |
| 5-SO₂CH₃ | 3-C₂H₅ | 4-C₂H₅ | H | H | OCH₃ | |
| 4-SO₂C₂H₅ | H | H | C₃H₇ | H | Cl | |
| 4-SO₂CH₃ | 5-CH₃ | H | H | H | CH₃ | |
| 3-SO₂CH₃ | H | H | H | OCH₃ | CH₃ | |
| 3-COCH₃ | H | 5-CH₃ | CH₃ | H | CH₃ | |
| 3-COC₃H₇ | H | H | H | CH₃ | CH₃ | |
| 4-COCH₃ | 5-CH₃ | H | H | H | CH₃ | |
| 5-COC₄H₉ | H | 3-Br | cyclohexyl | CH₃ | Cl | |
| 5-COCH₃ | H | 3-Cl | H | H | Cl | |
| 5-COCH₃ | H | H | CH₃ | H | Cl | |
| 5-CO₂C₂H₅ | H | 3-Br | CH₃ | H | Cl | |
| 5-CO₂CH₃ | H | 3-Cl | H | H | Cl | |
| 5-CO₂CH₃ | H | H | H | H | Cl | |
| 5-COC₄H₉ | 3-C₂H₅ | H | i-C₃H₇ | H | OCH₃ | |
| 3-CO₂CH₃ | H | H | CH₃ | CH₃ | OCH₃ | |
| 4-CO₂C₃H₇ | H | 5-C₄H₉ | H | OCH₃ | OCH₃ | |
| 5-CO₂H | H | 3-Cl | H | H | CH₃ | |
| 5-CO₂H | 3-CH₃ | 4-CH₃ | H | OCH₃ | OC₂H₅ | |
| 3-CO₂H | 4-C₂H₅ | 5-C₂H₅ | cyclohexyl | H | OCH₃ | |
| 4-CO₂H | H | H | H | CH₃ | CH₃ | |

TABLE VII

| R₁ | R₂ | R₃ | R₄ | R₉ | Y¹ | m.p. (°C.) |
|---|---|---|---|---|---|---|
| H | H | H | H | H | H | |
| H | H | H | H | H | CH₃ | |
| H | H | H | H | H | Cl | |
| H | H | H | CH₃ | H | OCH₃ | |
| H | H | H | t-C₄H₉ | CH₃ | OCH₂CH₃ | |
| H | H | H | cyclohexyl | OCH₃ | OCH₃ | |

TABLE VII-continued

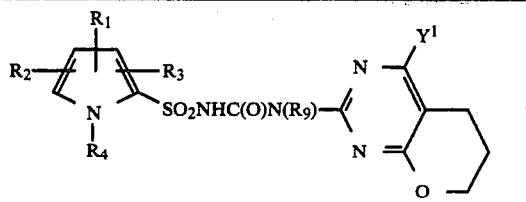

| R₁ | R₂ | R₃ | R₄ | R₉ | Y¹ | m.p. (°C.) |
|---|---|---|---|---|---|---|
| H | H | H | (CH₂)₂CN | H | CH₃ | |
| H | H | H | CH₂C₆H₅ | H | CH₃ | |
| H | H | H | o-ClC₆H₄ | CH₃ | CH₃ | |
| 5-CH₃ | H | H | COCH₃ | H | CH₃ | |
| 5-C₄H₉ | 3-CH₃ | H | CONMe₂ | H | CH₃ | |
| H | 3-C₂H₅ | H | CO₂C₂H₅ | H | CH₃ | |
| H | H | H | COC₄H₉ | H | OCH₃ | |
| 4-CH₃ | 5-CH₃ | H | H | H | OCH₃ | |
| 5-C₄H₉ | H | H | H | CH₃ | CH₃ | |
| H | 3-C₂H₅ | 4-C₂H₅ | p-NO₂C₆H₄ | H | CH₃ | |
| H | 3-CH₃ | 4-C₃H₇ | H | CH₃ | CH₃ | |
| CH₃ | CH₃ | CH₃ | H | OCH₃ | OCH₃ | |
| H | 4-CH₃ | 5-C₂H₅ | ⬡ | H | OCH₃ | |
| 5-NO₂ | H | H | H | H | OCH₃ | |
| 5-NO₂ | 3-CH₃ | 4-CH₃ | H | OCH₃ | Cl | |
| 5-NO₂ | H | 3-Br | H | H | Cl | |
| 4-NO₂ | H | 5-C₃H₇ | H | CH₃ | Cl | |
| 3-NO₂ | H | H | H | H | H | |
| 5-CN | H | 3-Cl | H | H | H | |
| 5-CN | 3-CH₃ | 4-CH₃ | H | OCH₃ | H | |
| 4-CN | H | H | ⬡ | H | OC₂H₅ | |
| 3-CN | H | H | (CH₂)₂CN | H | OC₂H₅ | |
| 5-SO₂CH₃ | H | 3-Br | H | H | OC₂H₅ | |
| 5-SO₂C₃H₇ | H | H | H | H | CH₃ | |
| 5-SO₂CH₃ | 3-C₂H₅ | 4-C₂H₅ | H | H | OCH₃ | |
| 4-SO₂C₂H₅ | H | H | C₃H₇ | H | Cl | |
| 4-SO₂CH₃ | 5-CH₃ | H | H | H | CH₃ | |
| 3-SO₂CH₃ | H | H | H | OCH₃ | CH₃ | |
| 3-COCH₃ | H | 5-CH₃ | CH₃ | H | CH₃ | |
| 3-COC₃H₇ | H | H | H | CH₃ | CH₃ | |
| 4-COCH₃ | 5-CH₃ | H | H | H | CH₃ | |
| 5-COC₄H₉ | H | 3-Br | ⬡ | CH₃ | Cl | |
| 5-COCH₃ | H | 3-Cl | H | H | Cl | |
| 5-COCH₃ | H | H | CH₃ | H | Cl | |
| 5-CO₂C₂H₅ | H | 3-Br | CH₃ | H | Cl | |
| 5-CO₂CH₃ | H | 3-Cl | H | H | Cl | |
| 5-CO₂CH₃ | H | H | H | H | Cl | |
| 5-COC₄H₉ | 3-C₂H₅ | H | i-C₃H₇ | H | OCH₃ | |
| 3-CO₂CH₃ | H | H | CH₃ | CH₃ | OCH₃ | |
| 4-CO₂C₃H₇ | H | 5-C₄H₉ | H | OCH₃ | OCH₃ | |
| 5-CO₂H | H | 3-Cl | H | H | CH₃ | |
| 5-CO₂H | 3-CH₃ | 4-CH₃ | H | OCH₃ | OC₂H₅ | |
| 3-CO₂H | 4-C₂H₅ | 5-C₂H₅ | ⬠ | H | OCH₃ | |
| 4-CO₂H | H | H | H | CH₃ | CH₃ | |

TABLE VIII $$\text{[Structure: pyrrole with } R_1, R_2, R_3 \text{ substituents, } N-R_4, \text{ connected via } SO_2NHC(O)N(R_9)\text{— to pyrimidine with } Y^1, \text{ fused furan with } CH_3]$$

| $R_1$ | $R_2$ | $R_3$ | $R_4$ | $R_9$ | $Y^1$ | m.p. (°C.) |
|---|---|---|---|---|---|---|
| H | H | H | H | H | H | |
| H | H | H | H | H | $CH_3$ | |
| H | H | H | H | H | Cl | |
| H | H | H | $CH_3$ | H | $OCH_3$ | |
| H | H | H | $t\text{-}C_4H_9$ | $CH_3$ | $OCH_2CH_3$ | |
| H | H | H | cyclohexyl | $OCH_3$ | $OCH_3$ | |
| H | H | H | $(CH_2)_2CN$ | H | $CH_3$ | |
| H | H | H | $CH_2C_6H_5$ | H | $CH_3$ | |
| H | H | H | $o\text{-}ClC_6H_4$ | $CH_3$ | $CH_3$ | |
| 5-$CH_3$ | H | H | $COCH_3$ | H | $CH_3$ | |
| 5-$C_4H_9$ | 3-$CH_3$ | H | $CONMe_2$ | H | $CH_3$ | |
| H | 3-$C_2H_5$ | H | $CO_2C_2H_5$ | H | $CH_3$ | |
| H | H | H | $COC_4H_9$ | H | $OCH_3$ | |
| 4-$CH_3$ | 5-$CH_3$ | H | H | H | $OCH_3$ | |
| 5-$C_4H_9$ | H | H | H | $CH_3$ | $CH_3$ | |
| H | 3-$C_2H_5$ | 4-$C_2H_5$ | $p\text{-}NO_2C_6H_4$ | H | $CH_3$ | |
| H | 3-$CH_3$ | 4-$C_3H_7$ | H | $CH_3$ | $CH_3$ | |
| $CH_3$ | $CH_3$ | $CH_3$ | H | $OCH_3$ | $OCH_3$ | |
| H | 4-$CH_3$ | 5-$C_2H_5$ | cyclohexyl | H | $OCH_3$ | |
| 5-$NO_2$ | H | H | H | H | $OCH_3$ | |
| 5-$NO_2$ | 3-$CH_3$ | 4-$CH_3$ | H | $OCH_3$ | Cl | |
| 5-$NO_2$ | H | 3-Br | H | H | Cl | |
| 4-$NO_2$ | H | 5-$C_3H_7$ | H | $CH_3$ | Cl | |
| 3-$NO_2$ | H | H | H | H | H | |
| 5-CN | H | 3-Cl | H | H | H | |
| 5-CN | 3-$CH_3$ | 4-$CH_3$ | H | $OCH_3$ | H | |
| 4-CN | H | H | cyclopentyl | H | $OC_2H_5$ | |
| 3-CN | H | H | $(CH_2)_2CN$ | H | $OC_2H_5$ | |
| 5-$SO_2CH_3$ | H | 3-Br | H | H | $OC_2H_5$ | |
| 5-$SO_2C_3H_7$ | H | H | H | H | $CH_3$ | |
| 5-$SO_2CH_3$ | 3-$C_2H_5$ | 4-$C_2H_5$ | H | H | $OCH_3$ | |
| 4-$SO_2C_2H_5$ | H | H | $C_3H_7$ | H | Cl | |
| 4-$SO_2CH_3$ | 5-$CH_3$ | H | H | H | $CH_3$ | |
| 3-$SO_2CH_3$ | H | H | H | $OCH_3$ | $CH_3$ | |
| 3-$COCH_3$ | H | 5-$CH_3$ | $CH_3$ | H | $CH_3$ | |
| 3-$COC_3H_7$ | H | H | H | $CH_3$ | $CH_3$ | |
| 4-$COCH_3$ | 5-$CH_3$ | H | H | H | $CH_3$ | |
| 5-$COC_4H_9$ | H | 3-Br | cyclohexyl | $CH_3$ | Cl | |
| 5-$COCH_3$ | H | 3-Cl | H | H | Cl | |
| 5-$COCH_3$ | H | H | $CH_3$ | H | Cl | |
| 5-$CO_2C_2H_5$ | H | 3-Br | $CH_3$ | H | Cl | |
| 5-$CO_2CH_3$ | H | 3-Cl | H | H | Cl | |
| 5-$CO_2CH_3$ | H | H | H | H | Cl | |
| 5-$COC_4H_9$ | 3-$C_2H_5$ | H | $i\text{-}C_3H_7$ | H | $OCH_3$ | |
| 3-$CO_2CH_3$ | H | H | $CH_3$ | $CH_3$ | $OCH_3$ | |
| 4-$CO_2C_3H_7$ | H | 5-$C_4H_9$ | H | $OCH_3$ | $OCH_3$ | |
| 5-$CO_2H$ | H | 3-Cl | H | H | $CH_3$ | |
| 5-$CO_2H$ | 3-$CH_3$ | 4-$CH_3$ | H | $OCH_3$ | $OC_2H_5$ | |
| 3-$CO_2H$ | 4-$C_2H_5$ | 5-$C_2H_5$ | cyclopentyl | H | $OCH_3$ | |
| 4-$CO_2H$ | H | H | H | $CH_3$ | $CH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IX

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, December 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

Wettable Powder

N-[(4-methoxy-6-methyl-1,3,5-triazin-2-yl)aminocarbonyl]-2,5-dimethyl-1H-pyrrole-3-sulfonamide: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 8

Wettable Powder

N-[(4,6-dimethylpyrimidin-2-yl)aminocarbonyl]-2,5-dimethyl-1H-pyrrole-3-sulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 9

Granule

Wettable Powder of Example 12: 5%
attapulgite granules (U.S.S. 20–40 mesh; 0.84–0.42 mm): 95%

A slurry of wettable powder containing ≈25% solids is sprayed on the surface of attapulgite granules in a double-cone blender. The granules are dried and packaged.

EXAMPLE 10

Extruded Pellet

N-[(4,6-dimethylpyrimidin-2-yl)aminocarbonyl]-1H-pyrrole-2-sulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

Oil Suspension

N-[(4-methoxy-6-methylpyrimidin-2-yl)aminocarbonyl]-1H-pyrrole-2-sulfonamide: 25%
polyoxyethylene sorbitol hexaoleate: 5%
highly aliphatic hydrocarbon oil: 70%

The ingredients are ground together in a sand mill until the solid particles have been reduced to under about 5 mirons. The resulting thick suspension may be applied directly, but preferably after being extended with oils or emulsified in water.

EXAMPLE 12

Wettable Powder

N-[(4-methoxy-6-methyl-1,3,5-triazin-2-yl)aminocarbonyl]-2,5-dimethyl-1H-pyrrole-3-sulfonamide: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

Low Strength Granule

N-[(4,6-dimethylpyrimidin-2-yl)aminocarbonyl]-1-methyl-1H-pyrrole-X-sulfonamide; (X indicates mixtures of pyrrole-2- and pyrrole-3-sulfonamides): 1%
N,N-dimethylformamide: 9%
attapulgite granules: (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 14

Aqueous Suspension

N-[(4,6-dimethylpyrimidin-2-yl)aminocarbonyl]-1-(phenylmethyl)-1H-pyrrole-X-sulfonamide, (X indicates mixtures of pyrrole-2- and pyrrole-3-sulfonamides): 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 15

Solution

X-[((4,6-dimethylpyrimidin-2-yl)aminocarbonyl)aminosulfonyl]-1-methyl-1H-pyrrole-2-carboxylic acid, methyl ester, (X indicates mixtures of 4- and 5-substituents), sodium salt: 5%
water: 95%

The salt is aded directly to the water with stirring to produce the solution, which may then be packaged for use.

EXAMPLE 16

Low Strength Granule

N-[(4,6-dimethylpyrimidin-2-yl)aminocarbonyl]-X-nitro-1H-pyrrole-2-sulfonamide, (X indicates mixtures of 3- and 4-substituents): 0.1%
attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

Granule

4-[((4,6-dimethylpyrimidin-2-yl)aminocarbonyl)aminosulfonyl]-1H-pyrrole-2-carboxylic acid, methyl ester: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

EXAMPLE 18

High Strength Concentrate

5-[((4,6-dimethylpyrimidin-2-yl)aminocarbonyl)aminosulfonyl]-4-bromo-1H-pyrrole-2-carboxylic acid, methyl ester: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 19

Wettable Powder 4-bromo-5-[((4,6-dimethylpyrimidin-2-yl)aminocarbonyl]aminosulfonyl)-1-methyl-1H-pyrrole-2-carboxylic acid, ethyl ester: 90%
dioctyl sodium sulfosuccinate: 0.1%
synthetic fine silica: 9.9%

The ingredients are blended and ground in a hammer-mill to produce particles essentially all below 100 mirons. The material is sifted through a U.S.S. No. 50 screen and then packaged.

EXAMPLE 20

Wettable Powder

X-[((4-methoxy-6-methyl-1,3,5-triazin-2-yl)aminocarbonyl)aminosulfonyl]-1H-pyrrole-2-carboxylic acid, methyl ester (X indicates mixtures of 4- and 5-substituents): 40% sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 21
Oil Suspension

N-[(4,6-dimethylpyrimidin-2-yl)aminocarbonyl]-1H-pyrrole-2-sulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, compounds of this invention may also be used to modify plant growth beneficially; some of the compounds may be used to selectively control weeds in crops such as wheat, barley, cotton and soybeans.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used as levels of about 0.01 to 20 kg/ha with a preferred range of 0.03 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosphonomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl)acetanilide (alachlor); 1,1-dimethyl-3-(α,α,α-trifluoro-m-tolyl)-urea (fluometuron); and 5-[2-chloro-4-(trifluoromethyl)phenoxy]-2-nitrobenzoic acid, methyl ester (acifluorfen-methyl).

The activity of these compounds was discovered in greenhouse tests. The tests are described and data resulting from them are shown below.

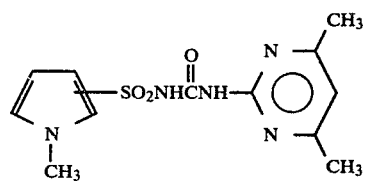

Compound 1 mixture of 2- and 3-isomers

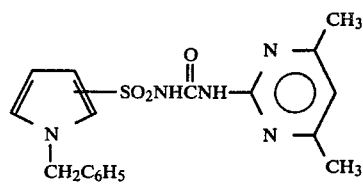

Compound 2 mixture of 2- and 3-isomers

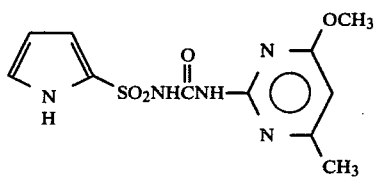

Compound 3

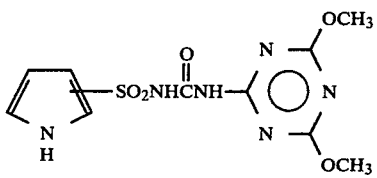

Compound 4 mixture of 2- and 3-isomers

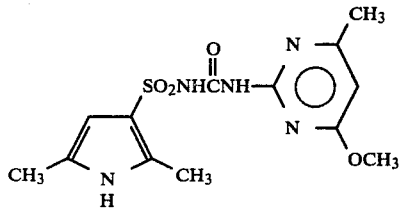

Compound 5

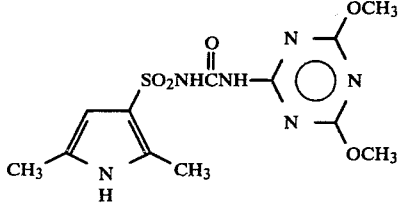

Compound 6

-continued

Compound 7
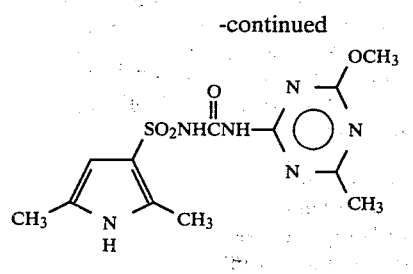

Compound 8
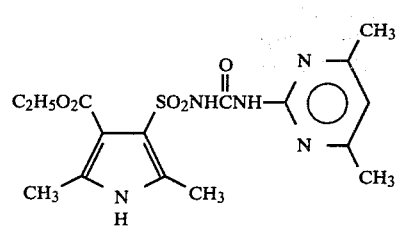

Compound 9
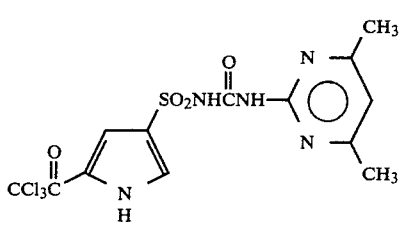

Compound 10
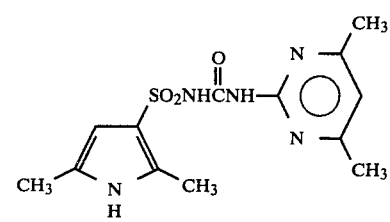

Compound 11
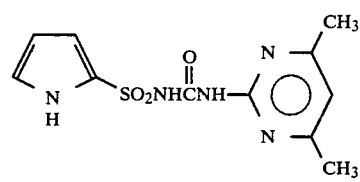

Compound 12
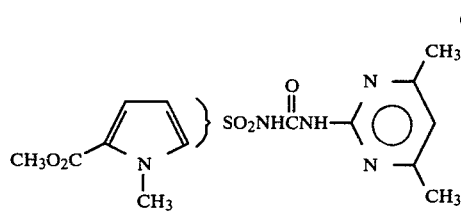
mixture of 4- and 5-isomers

Compound 13
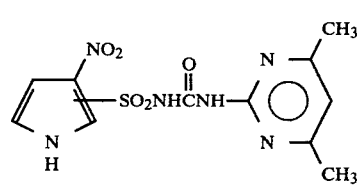
mixture of 2- and 5-isomers

-continued

Compound 14

Compound 15

Compound 16
mixture of 4- and 5-isomers

Compound 17

Compound 18

Compound 19

Test A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium spp.), sorghum, corn, soybean, rice, wheat and nutsedge tubers (Cyperus rotundus) were planted in a growth medium and treated pre-emergence with the chemicals dissolved in a nonphytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum and corn with three leaves, soybean with two cotyledonary leaves, rice with two leaves, wheat with two leaves, and nutsedge with three to five leaves were sprayed. Treated plants and controls were maintained in a greenhouse for sixteen days, then all species were compared to controls and visually rated for response to treatment as recorded in Table A.

The ratings are based on a numerical scale extending from 0=no injury, to 10=complete kill. The accompanying descriptive symbols have the following meanings:
G=growth retardation;
C=chlorosis/necrosis;
E=emergence inhibition;
H=formative effects;
6Y=flowerbuds abscised;
U=unusual pigmentation;
A=accelerated growth;
6F=delayed flowering; and
X=axillary stimulation.

TABLE A

| | Compound 1 | Compound 2 | Compound 3 | Compound 4 | Compound 5 | Compound 6 | Compound 7 | Compound 8 | Compound 9 | Compound 10 | Compound 11 | Compound 12 |
|---|---|---|---|---|---|---|---|---|---|---|---|---|
| Rate kg/ha | 0.4 | 0.4 | 0.4 | 0.4 | 0.4 | 0.4 | 0.4 | 0.4 | 0.4 | 0.4 | 0.05 | 0.4 |
| POST-EMERGENCE | | | | | | | | | | | | |
| Bush bean | 7C,9G | 7C,9G | 7C,6G,6Y | 8C,7G | 5C,6G,6F | 4C,6G,6Y | 9C,8G | 0 | 2G | 3C,9G,6Y | 6C,9G,6Y | 6C,9G,6Y |
| Cotton | 4C,9G | 3C,4G | 7C,6G | 7C,6G | 2C,3G | 3G | 2G | 0 | 0 | 2C,2H | 3C,6H | 4C,9G |
| Morningglory | 6C,9G | 2C,7G | 10C | 10C | 2C,3G | 2C,3G | 5C,4G | 0 | 0 | 3C,5G | 5C,9G | 6C,9G |
| Cocklebur | 5C,9G | 2C,7G | 5C,5G | 7C,7G | 2G | 2G | 2C,2G | 0 | 5G,6F | 2C | 9C | 6C,9G |
| Cassia | 2C,4H | 2C,7G | 7C,6G | 8C,7G | 0 | 0 | 3G | 0 | 2A | 2C,9G | 9C | 6C,9G |
| Nutsedge | 7G | 4G | 7C,6G | 8C,5G | 0 | 0 | 3G | 0 | 0 | 3G | 6G | 5G |
| Crabgrass | 3C,6G | 3C,7G | 10C | 10C | 2C,3G | 2C,3G | 10C | 0 | 0 | 2C,8H | 9C | 3C,9G |
| Barnyardgrass | 9C | 3C,8H | 10C | 10C | 3C,3G | 5C,3G | 10C | 5C | 0 | 2C,8H | 2C,8H | 9C |
| Wild Oats | 5C,8G | 2C,7G | 10C | 7C,7G | 4C,3G | 5C,6G | 10C | 1C | 0 | 1C,3G | 6C,9G | 5C,8G |
| Wheat | 5C,9G | 2C,8G | 7C,6G | 6C,5G | 3C,3G | 2C,3G | 8C,6G | 0 | 0 | 8G,5X | 1C,8G | 5U,9G |
| Corn | 5U,9G | 1C,8G | 6C,5G | 10C | 0 | 2C,3U,4G | 7C,5G | 1C,2G | 0 | 2C,7G | 2C,9G | 7U,9G |
| Soybean | 9C | 1C,8G | 7C,6G | 7C,6G | 3C,4G | 0 | 4C,5G | 0 | 1H | 1C,2H | 9C | 9C |
| Rice | 9C | 2C,8G | 8C,6G | 8C,7G | 2C,3G | 2C,3G | 7C,6G | 2C,8G | 3G | 4G | 5C,8G | 5C,9G |
| Sorghum | 3C,9H | 1C,8G | 8C,6G | 7G,8G | 2C,3G | 4G | 8C,6G | 2C,8G | 2C,9G | 1C,9G | 2C,9G | 5C,9G |
| PRE-EMERGENCE | | | | | | | | | | | | |
| Morningglory | 9G | 9G | 7C,7G | 7C,6G | 4G | 5C,7G | 7G,7C | 0 | 0 | 7G | 4C,9H | 9G |
| Cocklebur | — | 8H | 3C,6G | 8C,6G | 5C,4G | 10C | 10C | 2C,2H | 0 | 8H | 4C,9H | 9H |
| Cassia | 8G | 2C,8G | 4C,6G | 8C,8G | 3C,5G | 7C,5G | 7C,6G | 1C | 0 | 7G | 4C,9G | 2C,9G |
| Crabgrass | 10E | 8G | 10E | 10E | 0 | 8C,8G | 10E | 2C,6G | 0 | 7G | 5C,9G | 10G |
| Barnyardgrass | 1C,5G | 3C,9H | 8C,8G | 7C,8G | 4G | 2C,5G | 5C,8G | 2C,5G | 0 | 2C,7G | 2C,8H | 8G,2C |
| Wild Oats | 9H | 2C,9H | 10C | 8C,9G | 7C,8G | 7C,7G | 10C | 3C,8H | 0 | 9H | 4C,9H | 2C,9H |
| Wheat | 1C,8H | 2C,7G | 8C,7G | 7C,6G | 7C,6G | 5C,6G | 7C,7G | 2C,9G | 0 | 2C,8G | 5C,9H | 3C,9G |
| Corn | 1C,8G | 2C,9H | 10E | 7C,8G | 8C,8G | 7C,8G | 10C | 2C,9G | 0 | 1C,9G | 9H | 3C,9G |
| Soybean | 3C,9G | 2C,9G | 10E | 7C,6G | 7C,6G | 7C,6G | 8C,8G | 0 | 0 | 1C,9G | 5C,9H | 2C,5H |
| Rice | 7H | 4H | 9H,9G | 10E | 7C,8G | 10E | 10C | 3C,9G | 0 | 3H | 3C,8H | 10E |
| Sorghum | 10E | 9H | 10E | 10E | 7C,8G | 10E | 10C | 3C,9G | 0 | 7G | 9H | 5U,9G |
| | 3C,9H | 2C,9H | 10E | 7G,8G | 10E | 8C,8G | 10C | 3C,9G | 0 | 1C,9G | 10H | 5C,9H |

| | Compound 13 | Compound 14 | Compound 15 | Compound 16 | Compound 17 | Compound 18 | Compound 19 |
|---|---|---|---|---|---|---|---|
| Rate kg/ha | 0.4 | 0.4 | 0.4 | 0.4 | 0.4 | 0.4 | 0.05 |
| POST-EMERGENCE | | | | | | | |
| Bush bean | 2C,6F | 5C,8G,6Y | 6C,9G,6Y | 9C | 3C,7G,6Y | 3C,9G,6Y | 3C,6Y |
| Cotton | — | 5C,8G | 2C,8G | 5C,9G | 2C | — | 1C |
| Morningglory | 4C,8G | 9C | 2C,6G | 9C | 1C | 3G | 1C,3H |
| Cocklebur | 3C,6G | 3C | 4C,9G | 10C | 2C,5G | 9C | 2C |
| Cassia | 3C,6G | 10E | 2C,3H | 6C,9G | 1C | 1C | 1C |
| Nutsedge | 8G | 5C,9G | 2C,5G | 3C,9G | 0 | 2G | 2G |
| Crabgrass | 4C,9G | 2C,9G | 3C,8G | 9G | 0 | 4C,9G | 2C,5G |
| Barnyardgrass | 5C,9H | 2C,9H | 5C,9H | 9C | 1H | 5C,9H | 3G |
| Wild Oats | 7G | 2C,9G | 2C,9G | 9C | 0 | 4C,8G | 4G |
| Wheat | 2C,8G | 2C,8G | 3C,9G | 6C,9G | 0 | 3C,8G | 4G |
| Corn | 6U,9G | 4U,9G | 9C | 9C | 3C,8H | 5C,9H | 1C,4H |
| Soybean | 2C,8G | 3C,9G | 9C | 5C,9H | 1H | 1H | 2C,2H |
| Rice | 6C,9G | 3C,9G | 2C,9G | 6C,9G | 2C,8G | 6C,9G | 8G |
| Sorghum | 6C,9G | 3C,9G | 2C,9G | 6C,9G | 2C,9H | 4C,9G | 2C,9G |
| PRE-EMERGENCE | | | | | | | |
| Morningglory | 8G | 9G | 9G | 9C | 1C | 8G | 0 |

TABLE A-continued

| | | | | | | | |
|---|---|---|---|---|---|---|---|
| Cocklebur | 8H | 5H | 9H | 8H | 0 | 9H | 0 |
| Cassia | 7G | 3C | 5G | 9H | 0 | 8H | 0 |
| Nutsedge | 10G | 10E | 5G | 10E | 1C | 10E | 0 |
| Crabgrass | 5C,9H | 3C,6G | 1C | 6C,9H | 0 | 3G | 2G |
| Barnyardgrass | 5C,9H | 3C,8H | 4C | 6C,9H | 2C | 2C,9H | 0 |
| Wild Oats | 2C,7G | 2C,5G | 4G | 6C,9G | 0 | 2C,8G | 4G |
| Wheat | 3C,9H | 9H | 3G | 9H | 0 | 9H | 2C,4G |
| Corn | 2C,9G | 2C,9H | 8G | 10E | 0 | 3C,9H | 0 |
| Soybean | 2G | 2C,2H | 3H | 9H | 0 | 4H | 6G |
| Rice | 10E | 9H | 9H | 10E | 0 | 10E | 0 |
| Sorghum | 10H | 2C,9H | 2C,9H | 6C,9H | 2G | 2C,9H | 3C,6G |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B

| Rate kg/ha | Compound 10 0.5 | Compound 11 0.06 | 0.06 | 0.13 | 0.25 | 0.25 | Compound 1 0.03 | 0.13 | Compound 3 0.02 | 0.5 | Compound 12 0.13 | Compound 13 0.13 | Compound 18 0.25 |
|---|---|---|---|---|---|---|---|---|---|---|---|---|---|
| Crabgrass | 2G | 8G | 5G | 6G,2C | 9G,6C | 6G | 0 | 0 | 6G | 9G,8C | 4G | 3G | 0 |
| Barnyardgrass | 4G | 4G | 0 | 5G,4C | 9G,9C | 3G | 0 | 0 | 6G,3H | 10C | 7G,3H | 2G | 3C |
| Sorghum | 9G,5H | 8G,5H | 10E | 10C | 9G,9C | 10C | 3G | 8G,5H | 9G,9C | 10E | 9G,5H | 8G,5H | 5G,3H |
| Wild Oats | 6G | 6G,2C | 0 | 7G,4C | 7G,7C | 7G,4C | 0 | 5G | 3G | 8G,6C | 7G | 2G | 6G,3H |
| Johnsongrass | 7G,3H | 7G,5H | 8G,4C | 7G,3C | 8G,5H | 8G,8C | 0 | 3G | 6G,3H | 9G,8C | 6G,3H | 4G,3H | 5G,2H |
| Dallisgrass | 3G | 8G | 5G | 6G | 8G | 9G,9C | 0 | 0 | 4G | 9G,5H | 4G,3H | — | 3G |
| Giant Foxtail | 7G,5C | 7G,3H | 4G | 7G,5C | 9G,9C | 8G,5H | 0 | 0 | 6G,3H | 10C | 3G | 4G,3H | 4G,2H |
| Ky. bluegrass | 6G,5C | 5G | 0 | 6G,3C | 7G,3C | 6G | 0 | 5G | 6G | 9G,8C | 4G | 2G | 6G,2H |
| Cheatgrass | 8G,8C | 7G | 10E | 9G,8C | 10E | 10E | 4G | 7G,2C | 7G,8C | 10E | 8G,5H | 7G,5E | 8G,5E |
| Sugarbeets | 5G | 7G,7C | 3G | 7G,5C | 9G,9C | 5G,5C | 3G | 8G,5C | 4G | 10C | 7G,8C | — | 8G,7C |
| Corn | 0 | 3G,3H | 0 | 9G,9C | 9G,9C | 5G,2H | 0 | 1C | 4G | 9G,9C | 2H | 0 | 7G,5H |
| Mustard | 8G | 8G | 8G | 8G,5C | 9G,8C | 9G,5C | 7G,3C | 8G,6C | 8G,8C | 10C | 8G,5C | 7G,3C | 7G,5C |
| Cocklebur | 0 | 6G,3H | 0 | 4G,2C | 8G,5H | 4G,3H | 0 | 0 | 0 | 8G,5H | 0 | 2G | 7G,3C |
| Pigweed | 3G | 7G | 4G | — | 10E | 9G,8C | 0 | 2G | 9G,9C | 10E | — | — | 6G |
| Nutsedge | 0 | 6G | 0 | 10E | 10E | 0 | 3G | 7G,3C | 0 | 10E | 0 | 5G | 8G |
| Cotton | 2G | 0 | 0 | 2H | 4G,3H | 2H | 0 | 0 | 0 | 7G,5H | 3G,3H | 3G | 5G |
| Morningglory | 3G | 6G | 0 | 7G | 8G | 3G | 0 | 5G | 6G | 9G,8C | 3H | 3G | 5G |
| Cassia | — | — | 5G | 8G | — | 9G,5H | 3G | 5G | 6G | 9G,5C | 5G,3H | 3G | 6G |
| Teaweed | 4G | 2G | 0 | 5G | 7G,3C | 0 | 0 | 5G | 3G | 7G,6C | 3G | 0 | 4G |
| Velvetleaf | 4G,3H | 6G,3H | 0 | 7G,5H | 8G,5H | 3G,5H | 0 | 5G,3H | 4G,2H | 9G,9C | 7G,5H | 3G | 6G,3H |
| Jimsonweed | 0 | 5G | 0 | 3G | 7G | 4G | 0 | 3G | 4G | 9G,9C | 4G | — | 4G |
| Soybean | 0 | 3G,2H | 0 | 0 | 7G,5H | 2H | 0 | 0 | 0 | 8G,3H | 5G,3H | 0 | 6G,3H |
| Rice | 7G,3C | 7G,5E | 6G,3C | 10C | 10E | 8G,8C | 5G | 8G,8C | 7G,5C | 10E | 10C | 8G,5H | 10E |
| Wheat | 4G | 4G,5E | 3G | 6G,4C | 8G,9E | 7G,3C | 0 | 3G | 3G | 8G,8C | 4G | 0 | 5G,2H |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table C.

TABLE C

Over-the-Top Soil/Foliage Treatment

| Rate kg/ha | Compound 3 0.25 | 0.06 | Compound 4 0.25 | 0.06 | Compound 7 0.25 | Compound 1 0.12 | Compound 11 0.12 | 0.03 |
|---|---|---|---|---|---|---|---|---|
| Soybeans | 10G, 6C | 10G, 5C | 9G, 9C | 8G, 2C | 9G, 9C | 9G, 5C | 10G, 7C | 10G, 7C |
| Velvetleaf | 7G, 3C | 4G, 2C | 8G, 5C | 4G, 2C | 5G, 2C | 10G, 5C | 9G, 6C | 9G, 5C |
| Sesbania | 10G, 9C | 10G, 7C | 9G, 9C | 6G | 6G, 4C | 9G, 4C | 10G, 8C | 10G, 5C |
| Cassia | 10G, 5C | 8G, 4C | — | 8G, 4C | 6G | 7G, 3C | 10G, 8C | 10G, 7C |
| Cotton | 7G, 3C | 5G, 3C | 6G, 4C | 3G, 4C | 4G | 4G, 2C | 8G, 6C | 6G, 3C |
| Morningglory | 8G, 3C | 7G, 4C | 8G, 4C | 7G | 6G | 7G, 3C | 10G, 7C | 8G, 4C |
| Alfalfa | 5C | 5G, 3C | — | — | 3G | 3G, 2C | 9G, 4C | 6G, 3C |
| Jimsonweed | 10G, 5C | 5G, 2C | — | 0 | 5G | 4G, 2C | 7G, 2C | 3G, 3C |
| Cocklebur | 10G, 4C | 7G, 2C | 2G | 0 | 8G | 8G, 3C | 10G, 8C | 10G, 6C |
| Corn | 9G, 5U | 8G, 3U | 8G, 7U | 6G, 7U | 10C | 9G, 4C | 9G, 5C | 9G, 5C |
| Crabgrass | 8G, 4C | 5G, 3C | 9G, 9C | 8G, 7C | 7G | 2G | 10G, 8C | 9G, 5C |
| Rice | 8G, 3C | 7G, 3C | 8G, 8C | 8G, 8C | 8G, 6C | 8G, 5C | 8G, 5C | 8G, 4C |
| Nutsedge | 5C, 5G | 5G, 3C | 5G | 0 | 7G, 3C | 7G, 2C | 9G | 8G |
| Barnyardgrass | 9G, 7C | 7G, 7H | 10C | 10C | 9G, 9C | 2C, 8G | 9G, 4C | 7G, 3C |
| Wheat | 2C | 2C | 8G, 7C | 8G, 7C | 9G, 9C | 3G | 8G, 5C | 7G,4C |
| Giant foxtail | — | — | 8G, 7U | 10C | 7G, 5C | 6G, 2C | 9G, 5C | 7G, 3C |

TABLE C-continued

| | Over-the-Top Soil/Foliage Treatment | | | | | | | |
|---|---|---|---|---|---|---|---|---|
| | Compound 3 | | Compound 4 | | Compound 7 | Compound 1 | Compound 11 | |
| Rate kg/ha | 0.25 | 0.06 | 0.25 | 0.06 | 0.25 | 0.12 | 0.12 | 0.03 |
| Wild Oats | 7G, 3C | 4G | 7G, 6C | 8G, 7C | 7G, 5C | 5G | 9G, 5C | 9G, 3C |
| Sorghum | 8G, 4C | 7G, 3C | 5G, 9U | 5G, 7U | 8G, 6C | 9G, 5C | — | — |
| Yellow mustard | — | — | 8G, 8C | 8G | 10C | — | — | — |
| Pigweed | — | — | — | — | — | — | — | — |
| Johnsongrass | — | — | — | — | — | — | — | — |
| Sunflower | — | — | 6G | 3G | 8G, 3H | — | — | — |
| Sugarbeets | — | — | 9G, 9C | 8G | — | — | — | — |

What is claimed is:

1. A compound of the formula:

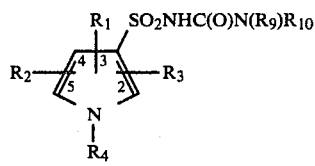

or

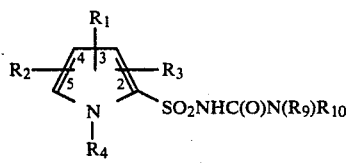

wherein $R_1$ is H, $C_1$-$C_4$ alkyl, $NO_2$, CN, $C(O)CCl_3$, $SO_2R_{11}$, $C(O)R_5$ or $CO_2H$;
$R_2$ is H or $C_1$-$C_4$ alkyl;
$R_3$ is H, $C_1$-$C_4$ alkyl, Cl or Br;
$R_4$ is H, $C_1$-$C_4$ alkyl, cyanoethyl, $C_5$-$C_6$ cycloalkyl, benzyl, phenyl substituted with Cl or $NO_2$, or $C(O)R_6$;
$R_5$ is $C_1$-$C_4$ alkyl or $C_1$-$C_4$ alkoxy;
$R_6$ is $C_1$-$C_4$ alkyl, $C_1$-$C_4$ alkoxy, or $NR_7R_8$;
$R_7$ and $R_8$ are independently $C_1$-$C_2$ alkyl;
$R_9$ is H, $CH_3$ or $OCH_3$;
$R_{11}$ is $C_1$-$C_4$ alkyl;
$R_{10}$ is

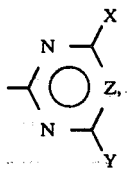

X is $CH_3$ or $OCH_3$;
Y is H, $CH_3$, $OCH_3$, $OCH_2CH_3$, $OCH_2CF_3$, Cl, $CH_2OCH_3$, and
Z is CH, $CCH_3$ $CCH_2CH_3$, $CCH_2CH_2Cl$, CCl, CBr or CF;

and their agriculturally suitable salts; provided that
(1) when $R_4$ is $C(O)R_6$, t-butyl or phenyl substituted with Cl or $NO_2$, then $R_1$ is H or $C_1$-$C_4$ alkyl and $R_1$, $R_2$ and $R_3$ cannot be s-butyl or isopropyl;
(2) $R_1$, $R_2$, $R_3$ and $R_{11}$ cannot be t-butyl;
(3) in Formula Ia, when $R_1$ is $NO_2$, then $R_1$ cannot be in the 5-position;
(4) in Formula Ia, when $R_1$ is not in the 5-position, $R_2$ and $R_3$ are other than H, and $R_1$ must be other than H unless both $R_2$ and $R_3$ are H;
(5) in Formula Ia, $R_3$ cannot be Cl or Br;
(6) in Formula Ib, $R_1$ cannot be $C(O)CCl_3$; and
(7) in Formula Ib, when $R_3$ is Cl or Br, then $R_3$ is in the 3-position and $R_1$ is in the 5-position and $R_1$ cannot be H or $C_1$-$C_4$ alkyl.

2. A compound of claim 1 wherein $R_9$ is H or $CH_3$.
3. A compound of claim 2 wherein $R_{10}$ is

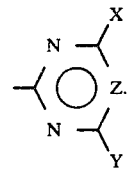

4. A compound of claim 3 wherein;
$R_5$ is $C_1$-$C_4$ alkoxy;
$R_2$ is H;
$R_4$ is H, $C_1$-$C_4$ alkyl or benzyl.
5. A compound of claim 4, structure Ia, wherein $R_1$ is H, $C_1$-$C_4$ alkyl or $COR_5$.
6. A compound of claim 4, structure Ib, wherein $R_1$ is H, $C_1$-$C_4$ alkyl, $NO_2$ or $COR_5$.
7. A compound of claim 5 wherein $R_1$ is in the 5 position.
8. A compound of claim 6 wherein $R_1$ is H, $NO_2$ or $COR_5$.
9. A compound of claim 7 wherein Y is $CH_3$, $OCH_3$ or $OCH_2CH_3$.
10. A compound of claim 8 wherein Y is $CH_3$, $OCH_3$ or $OCH_2CH_3$.
11. The compound of claim 1, N-[(4,6-dimethylpyrimidin-2-yl)aminocarbonyl]-2,5-dimethyl-1H-pyrrole-3-sulfonamide.
12. The compound of claim 1, N-[(4,6-dimethylpyrimidin-2-yl)aminocarbonyl]-1H-pyrrole-2-sulfonamide.
13. The compound of claim 1, N-[(4-methoxy-6-methylpyrimidin-2-yl)aminocarbonyl]-1H-pyrrole-2-sulfonamide.
14. The compound of claim 1, N-[(4,6-dimethylpyrimidin-2-yl)aminocarbonyl]-1-methyl-1H-pyrrole-X-sulfonamide; (X indicates mixtures of pyrrole-2- and pyrrole-3-sulfonamides).
15. The compound of claim 1, N-[(4,6-dimethylpyrimidin-2-yl)aminocarbonyl]-1-(phenylmethyl)-1H-pyrrole-X-sulfonamide; (X indicates mixtures of pyrrole-2- and pyrrole-3-sulfonamides).
16. The compound of claim 1, X-[((4,6-dimethylpyrimidin-2-yl)aminocarbonyl)aminosulfonyl]-1-methyl-1H-pyrrole-2-carboxylic acid, methyl ester; (X indicates mixtures of 4- and 5-substituents).

17. The compound of claim 1, N-[(4,6-dimethylpyrimidin-2-yl)aminocarbonyl]-X-nitro-1H-pyrrole-2-sulfonamide; (X indicates mixtures of 3- and 4-substituents).

18. The compound of claim 1, 4-[((4,6-dimethylpyrimidin-2-yl)aminocarbonyl)aminosulfonyl]-1H-pyrrole-2-carboxylic acid, methyl ester.

19. The compound of claim, 1,5-[((4,6-dimethylpyrimidin-2-yl)aminocarbonyl)aminosulfonyl]-4-bromo-1H-pyrrole-2-carboxylic acid, methyl ester.

20. The compound of claim 1, 4-bromo-5-[((4,6-dimethylpyrimidin-2-yl)aminocarbonyl)aminosulfonyl]-1-methyl-1H-pyrrole-2-carboxylic acid, ethyl ester.

21. A composition suitable for controlling the growth of undesired vegetation which comprises an effective amount of a compound of claim 1 and at least one of the following: surfactant, solid or liquid diluent.

22. A composition suitable for controlling the growth of undesired vegetation which comprises an effective amount of a compound of claim 2 and at least one of the following: surfactant, solid or liquid diluent.

23. A composition suitable for controlling the growth of undesired vegetation which comprises an effective amount of a compound of claim 3 and at least one of the following: surfactant, solid or liquid diluent.

24. A composition suitable for controlling the growth of undesired vegetation which comprises an effective amount of a compound of claim 4 and at least one of the following: surfactant, solid or liquid diluent.

25. A composition suitable for controlling the growth of undesired vegetation which comprises an effective amount of a compound of claim 5 and at least one of the following: surfactant, solid or liquid diluent.

26. A composition suitable for controlling the growth of undesired vegetation which comprises an effective amount of a compound of claim 6 and at least one of the following: surfactant, solid or liquid diluent.

27. A composition suitable for controlling the growth of undesired vegetation which comprises an effective amount of a compound of claim 7 and at least one of the following: surfactant, solid or liquid diluent.

28. A composition suitable for controlling the growth of undesired vegetation which comprises an effective amount of the compound of claim 8 and at least one of the following: surfactant, solid or liquid diluent.

29. A method for controlling the growth of undesired vegetation which comprises applying to the locus to be protected an effective amount of a compound of claim 1.

30. A method for controlling the growth of undesired vegetation which comprises applying to the locus to be protected an effective amount of a compound of claim 2.

31. A method for controlling the growth of undesired vegetation which comprises applying to the locus to be protected an effective amount of a compound of claim 3.

32. A method for controlling the growth of undesired vegetation which comprises applying to the locus to be protected an effective amount of a compound of claim 4.

33. A method for controlling the growth of undesired vegetation which comprises applying to the locus to be protected an effective amount of a compound of claim 5.

34. A method for controlling the growth the undesired vegetation which comprises applying to the locus to be protected an effective amount of a compound of claim 6.

35. A method for controlling the growth of undesired vegetation which comprises applying to the locus to be protected an effective amount of a compound of claim 7.

36. A method for controlling the growth of undesired vegetation which comprises applying to the locus to be protected an effective amount of the compound of claim 8.

* * * * *